United States Patent
Simmons, Sr.

(10) Patent No.: US 7,013,495 B2
(45) Date of Patent: Mar. 21, 2006

(54) REMOVABLE COMFORT SAFETY WING FOR USE WITH A SIDESHIELD

(75) Inventor: Bennie F. Simmons, Sr., Flower Mound, TX (US)

(73) Assignee: Safety Optical Service Co., Lewisville, TX (US)

( * ) Notice: Subject to any disclaimer, the term of this patent is extended or adjusted under 35 U.S.C. 154(b) by 0 days.

(21) Appl. No.: 10/923,340

(22) Filed: Aug. 20, 2004

(65) Prior Publication Data

US 2005/0018128 A1   Jan. 27, 2005

Related U.S. Application Data

(62) Division of application No. 10/355,702, filed on Jan. 31, 2003, now Pat. No. 6,832,389.

(51) Int. Cl.
*A61F 9/02* (2006.01)
(52) U.S. Cl. .................. 2/440; 2/13; 2/449; 2/431; 351/43; 351/158
(58) Field of Classification Search ............... 2/13, 2/449, 448, 431, 451, 12, 440; 351/44, 45, 351/47, 111, 158, 43
See application file for complete search history.

(56) References Cited

U.S. PATENT DOCUMENTS

| | | | |
|---|---|---|---|
| 2,172,573 A | 9/1939 | Blumenthal | |
| 2,422,534 A | 6/1947 | DuBois | |
| 2,840,821 A | 7/1958 | Gay, Jr. et al. | |
| 2,900,639 A | 8/1959 | Lindstrom | |
| 2,918,676 A * | 12/1959 | Matheson | 2/440 |
| 3,165,754 A | 1/1965 | Rodgers et al. | |
| 4,630,321 A | 12/1986 | Sagemuehl et al. | |
| 4,726,075 A | 2/1988 | Hinrichs | |
| 4,755,040 A * | 7/1988 | Haslbeck | 351/43 |
| 5,300,593 A | 4/1994 | Gardziella et al. | |
| 5,402,189 A | 3/1995 | Gill | |
| 5,548,351 A | 8/1996 | Hirschman et al. | |
| 5,608,469 A | 3/1997 | Bolle | |
| 5,748,278 A | 5/1998 | Simmons, Sr. | |
| 5,781,271 A | 7/1998 | Wheeler | |
| 5,798,815 A | 8/1998 | Hirschman et al. | |
| 6,062,688 A | 5/2000 | Vinas | |
| 6,247,811 B1 * | 6/2001 | Rhoades et al. | 351/156 |
| 6,282,727 B1 | 9/2001 | Lindahl | |
| RE37,530 E | 1/2002 | Hirschman et al. | |
| 6,393,609 B1 | 5/2002 | Simmons, Sr. | |
| 6,641,263 B1 * | 11/2003 | Olney | 351/62 |
| 2002/0029498 A1 | 3/2002 | Lindahl | |

* cited by examiner

*Primary Examiner*—Katherine Moran
*Assistant Examiner*—Richale L. Haney
(74) *Attorney, Agent, or Firm*—Rudolph J. Buchel, Jr.

(57) ABSTRACT

A sideshield eye protector is presented which includes a comfort and safety wing that is formed as a surface appendage thereon, and extends in a generally perpendicular direction from the surface of the sideshield along the contoured edge of the sideshield positioned closest to the wearer's face. The comfort and safety wing may be integral to the sideshield forming an integral structure therewith or removably attached thereto. The comfort and safety wing is oriented generally parallel with the facial surfaces and generally follows the proximate facial contours. A separate wing portion may be fabricated on both the upper and lower parts of each sideshield, the upper wing portion extending from the upper contoured edge of the sideshield which provides additional coverage over the upper portion of the eye orbits, temple and lower forehead area. The lower face about the lower eye orbit and upper cheek area has a generally parallel orientation with those facial surfaces.

75 Claims, 12 Drawing Sheets

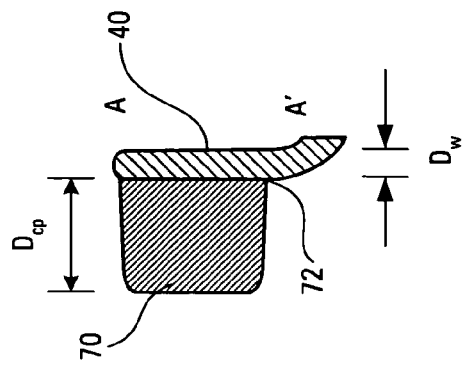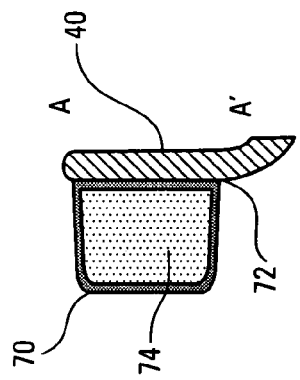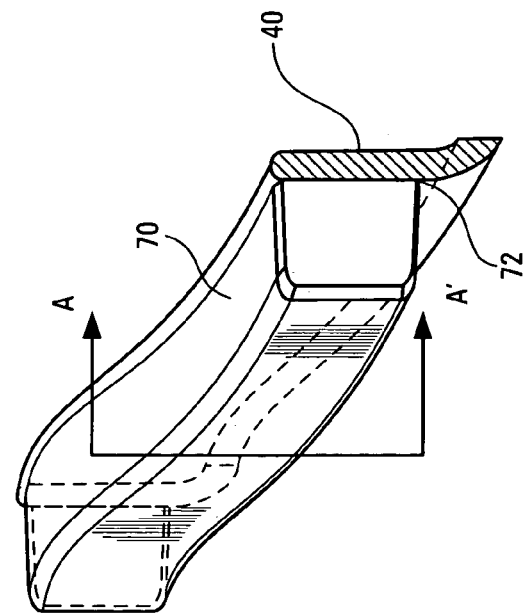

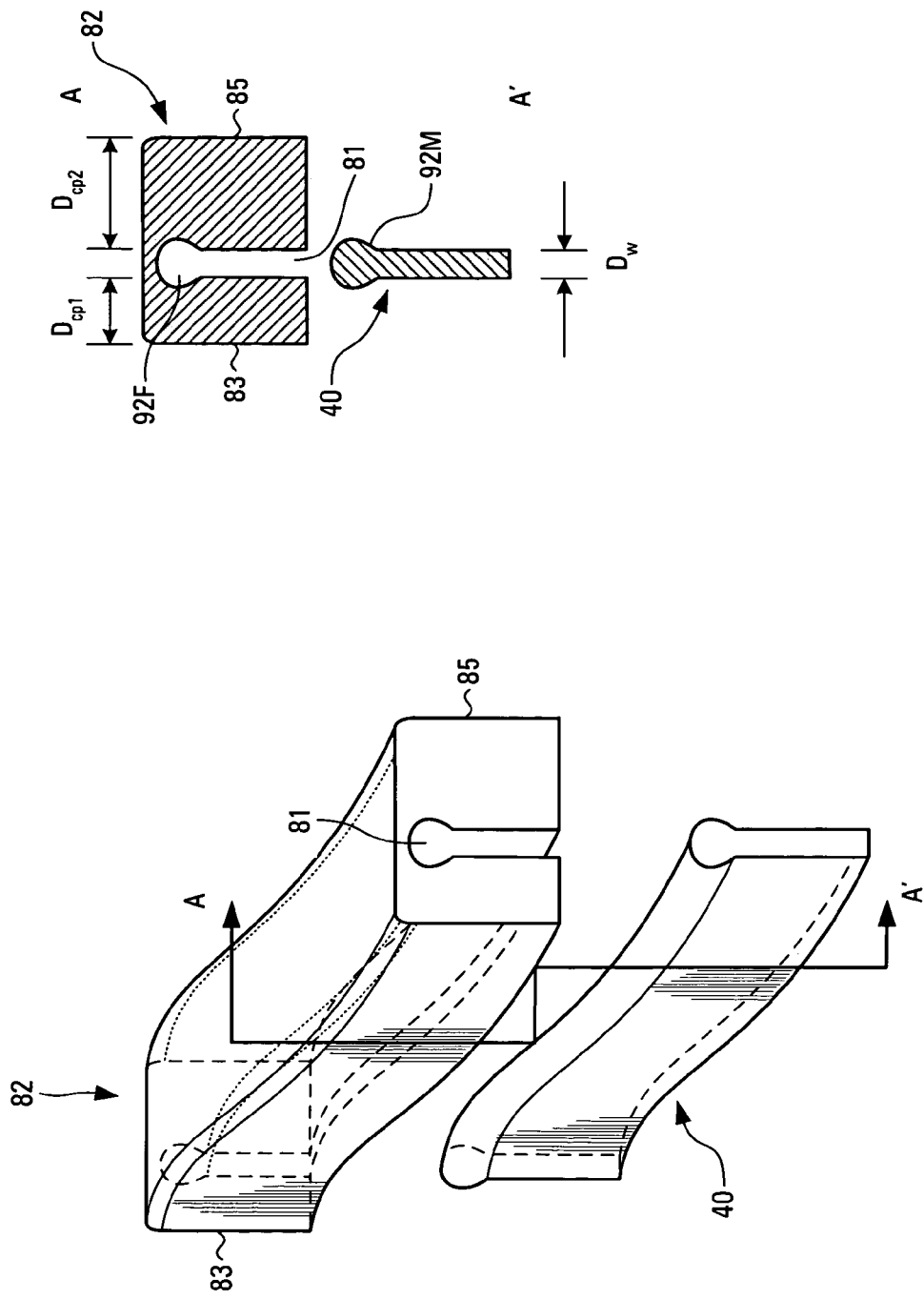

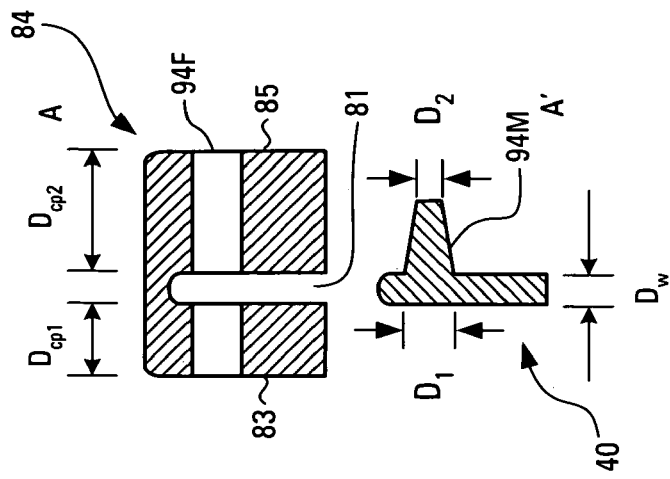
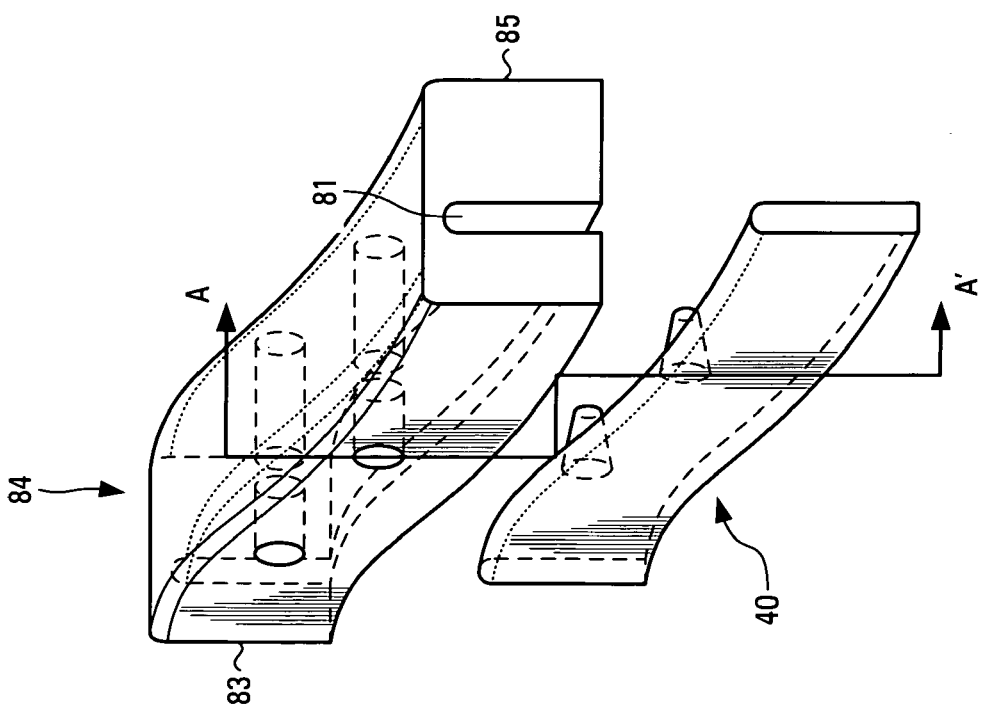

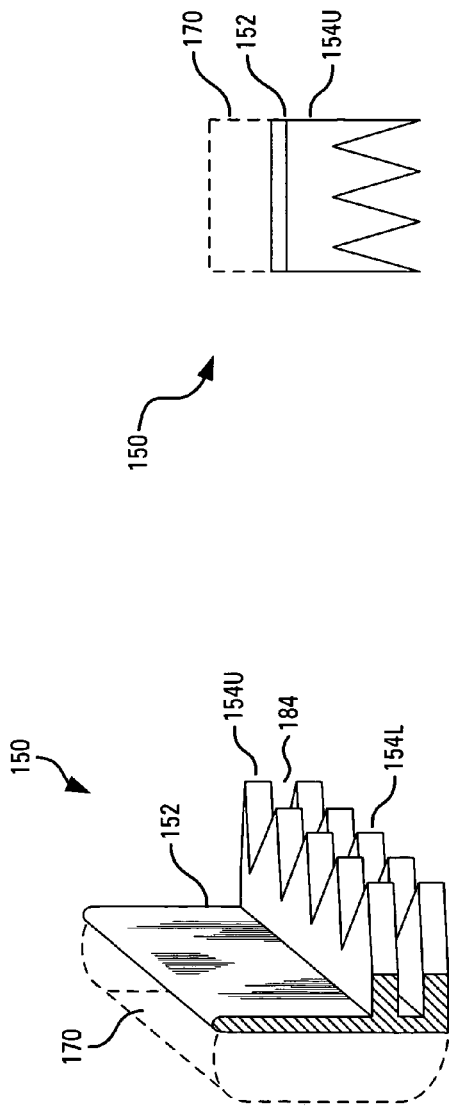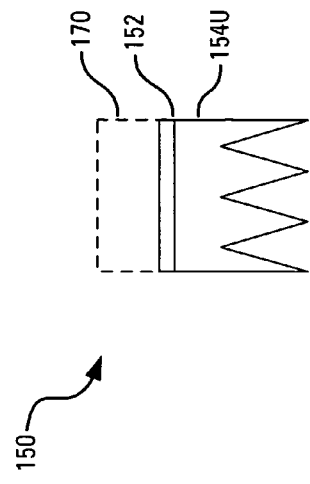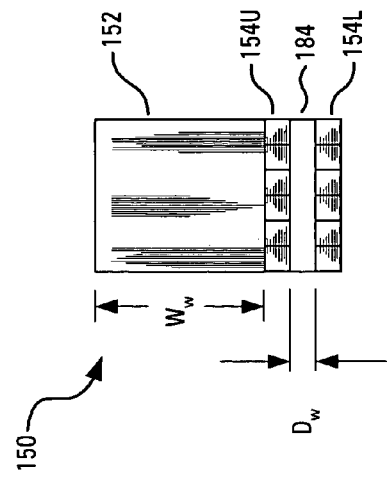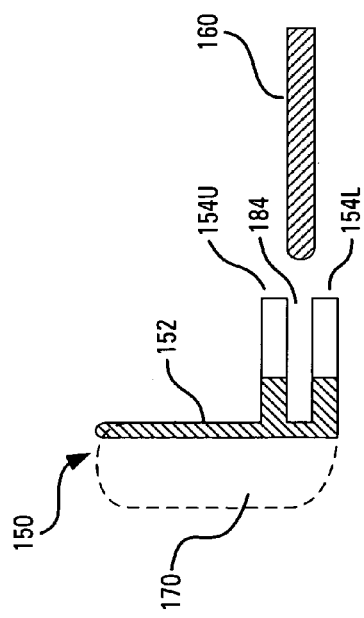

REMOVABLE COMFORT SAFETY WING FOR USE WITH A SIDESHIELD

This application is a division of U.S. patent application Ser. No. 10/355,702 filed Jan. 31, 2003, now U.S. Pat. No. 6,832,389 which is incorporated in its entirety herein by reference.

BACKGROUND OF THE INVENTION

1. Field of the Invention

The present invention relates in general to safety glasses which provide protection for the eyes from missiles originating from a frontal direction. More particularly, the present invention relates to eyewear with sideshield protection for reducing instances of eye injury from missiles originating from a lateral direction to the wearer. Still more particularly, the present invention relates to sideshield protection for reducing discomfort to the wearer from objects striking the eyewear.

2. Description of Related Art

Safety glasses are well known in the prior art and are used to protect the eyes of an individual from airborne particles, high-velocity projectiles, wind, and the like. As used herein, and by those skilled in the art, the terms "safety glasses" or "eyeshields" typically mean a protective barrier in front of the eye. A "sideshield," on the other hand, typically means a protective barrier to the side, above or below the eye which normally supplements safety glasses.

One relatively popular form of eye protection which incorporates side protection is commonly referred to as a "cover goggle." Generally, cover goggles are comprised of a soft plastic frame and a somewhat more resilient plastic mono lens. The cover goggles are usually held in place on the wearer's head by means of an elastic strap. Cover goggles can be worn as stand-alone eye protection or, advantageously, may be worn over standard prescription eyeglasses. An example of cover goggles is U.S. Pat. No. 2,422,534 to J. E. Du Bois titled "Eye Shield" which is incorporated herein by reference in its entirety.

As those skilled in the art of eyeglass and side shield manufacture are aware, the basic shapes of eyeglass frames are derived from a market which is fashion oriented and driven. Thus, cover goggles, while being an effective eye safety device, often go unused even when readily available due to the wearer's sense of fashion and vanity.

On the other hand, standard eyewear that incorporates safety sideshields are less bulky and intrusive for the user, and often more importantly to the user, present less of a fashion faux pas. Examples of sideshields for typical eyewear can be found in the following U.S. patents, each incorporated herein in their entirety: U.S. Pat. No. 5,748,278 issued May 5, 1998 to Bennie F. Simmons, Sr. and titled "Eyeglass Shield for Removable Attachment to Eyeglass Lens Frames"; U.S. Pat. No. 6,393,609 issued May 28, 2002 to Bennie F. Simmons, Sr. and titled "Protective Sideshield Removably Attachable to an Eyeglass Frame"; U.S. Pat. No. 5,798,815 issued Aug. 25, 1998 and corresponding U.S. Reissue Pat. No. RE37,530 E issued Jan. 29, 2002, both to Hirschman et al. and titled "Method and Kit for Attaching Side Shields to Eyeglass Temples"; U.S. Pat. No. 5,548,351 issued Aug. 20, 1996 to Hirschman et al. and titled "Method and Kit for Attaching Side Shields to Eyeglass Temples"; U.S. Pat. No. 5,781,271 issued Jul. 14, 1998 to Richard R. Wheeler and titled "Portable Safety Sideshields for Eye Glasses"; U.S. Pat. No. 5,608,469 issued on Mar. 4, 1997 to Maurice J. G. Bollé titled "Sunglasses with Removable Side Shields"; U.S. Pat. No. 5,402,189 issued Mar. 28, 1995 to Vicki L. Gill titled "Side Shield for Eyeglasses and Method of Making the Same"; U.S. Pat. No. 4,726,075 issued Feb. 23, 1988 to Matthew T. Hinrichs and titled "Disposable Side Shield for Eyeglasses"; U.S. Pat. No. 3,165,754 issued Jan. 19, 1965 to Rodgers et al. and titled "Side Shield Mounting for Spectacles"; U.S. Pat. No. 2,900,639 issued Aug. 25, 1959 to E. P. Lindstrom and titled "Spectacle Attachment"; U.S. Pat. No. 2,840,821 issued Jul. 1, 1958 to Gay, Jr. et al. and titled "Side Shield Attachment for Goggles and Spectacles"; and U.S. Pat. No. 6,062,688 issued May 16, 2000 to Joseph F. Vinas and titled "Detachable Eyeglass Foam Shield."

As may be apparent from the sideshields described in the above-identified patents, sideshields may be of various types. For example, some are permanently attached to the eyeglass frames and provide reasonable protection for the top, side, and bottom of the eye. Permanent sideshields have the advantage of being custom designed for accommodating a particular type of eyewear and offer the user an acceptable measure of protection, but usually little in the way of style. However, sideshields need not be permanently affixed to eyewear but instead may be temporary and removable. Removable sideshields are capable of being stored when not in use while the user may continue to wear the eyewear in a location not necessitating the use of safety sideshields. Removable sideshields have the advantage of being selectively affixed to the eyewear by the user. Sideshields that provide eye protection and which also fit a broad range of eyeglass frame shapes and sizes are known as universal sideshields. Universal sideshields have the further advantage of being fixably adaptable for fitting many types of eyewear and therefore may be made available for users at locations where sideshield protection is desirable but might not otherwise be available for a specific frame style and size. Moreover, universal sideshields enable users to couple the sideshields to fashion safety eyewear and thus maintain some semblance of style. Thus, eyewear used in conjunction with sideshields may be conventional safety glasses, with or without prescription lenses, or might instead be fashion safety eyewear, again, with or without prescription lenses.

As mentioned above, the basic shapes of safety eyeglass frames tend to follow dress or street wear fashion trends. As such, the frontal protective area is subject to wide fluctuations when on the one hand very large frames and lenses are in vogue and on the other when very narrow frames prevail with their inherently smaller lenses. As might be expected, narrow frames provide minimal frontal protection, yet are currently in high demand. Safety eyewear manufacturers quickly copy new trends in non-safety products for introduction into the industrial work place. This trend has resulted in the frames on safety glasses being somewhat narrowed thereby reducing the frontal protection afforded by current models of safety glasses.

The reduction in vertical frontal protection provided by the narrow frame and lenses adversely affects the lateral protection offered by side protectors, the sideshields. As may be understood from the prior art identified above, manufacturers have all but exhausted the shapes, configurations and methods of design and fabrication of sideshields. There are permanently affixed, detachable and universal versions of sideshields, as described immediately above. They may be designed to provide side protection only, side and top protection only, or the full cup style which provides roughly 180-degree protection, top-bottom-side. Those sideshields which provide side only, or side and top protection, generally incorporate flat, deflective or shock absorbing surfaces.

Cup or full sideshields are generally arcuate in shape and to a large degree must follow the basic design and shape of the eyeglass frame front.

All prior art sideshields have one thing in common: the vertical dimension of the eyeglass frames dictates the amount of lateral/vertical protection provided by the side protector.

The amount of the frontal protective area, horizontal or vertical, is not specified in the current version of the AMERICAN NATIONAL STANDARD Z87.1, Practice For Occupational and Educational Eye And Face Protection or in the pending major revision which is due for publication in late 2002 or early 2003. This revision specifies the locations at which a sideshield protector shall be impacted by a 0.25 in. (¼ inch) steel ball having been fired by an air gun at a velocity of 150 feet per second. These mandated tests are conducted upon safety eyewear devices which have been placed upon an Alderson $50^{th}$ percentile head form. The head form is adjusted such that the path of the projectile passes through the center of the anterior surface of either of the eyes of the head form. The head form is then rotated on an axis which passes vertically at the intersections of a sagital plane through the center of the front surface of the tested eye and a coronal (frontal) plane which is 10 mm (0.394 in.) posterior to the corneal plane which is tangent to the anterior surfaces of the eyes of the head form.

Testing of the sideshield is conducted while on the head form in the position previously described with the exception that the head form is rotated 90 degrees so as to properly position the sideshield for implementation of impact testing. Three impact locations are specified which utilize the center of the eye of the head form for reference:
1. impact the sideshield on a line which is on a plane with the center of the eye and 10 mm posterior to the center of the eye of the head form;
2. impact the sideshield 10 mm above and posterior to the center of the eye of the head form; and
3. impact the sideshield 10 mm below and posterior to the center of the eye of the head form.

Those skilled in the art of dispensing and adjusting eyeglasses to the wearer's head are keenly aware that the wearer's eyes, and those of the Alderson head form, will rarely be positioned at the mechanical center of the lenses of the eyeglasses frames. To the contrary, the frames are generally positioned through design of the frame, such that the eyes are located well above the mechanical center of the frames and lenses.

A typical fashion-oriented safety frame measures 35.63 mm (1.40 in.) vertically and the maximum side impact exposure area of the side shield is 28 mm (1.10 in.). Assuming that the frames, as worn, will rest with the mechanical center of the lens only 5 mm (0.197 inch) below the center of the eye, simple mathematics tells us that the high velocity ¼ inch steel ball will miss the sideshield and potentially strike the head form in the region of the eye cavity and upon an actual human head and would inflect serious injury if not causing death.

Another reality not considered in the present eyewear testing regime is the amount of force exerted on the wearer as a result of a projectile impact. Clearly, if the projectile test is successful, the wearer should not experience any eye injury. However, the kinetic energy transferred from the projectile to the eyeglasses or sideshield does not dissipate in the eyewear itself, but instead is transferred in substantial part to the wearer along contact surfaces of the safety device. Consequently, the wearer may experience discomfort at contact surfaces.

Inasmuch as OSHA, in its regulation 29 CFR Part 1910.133, relies heavily on ANSI Z87.1 for procedures in determining compliance, the industry will find itself with hundreds of thousands of safety glasses which have non-compliant sideshields attached. The average cost of over $100 per pair to replace those devices now in use would be astronomical, and in the current economy could prove catastrophic to the economic well being of some entities. An even more tragic scenario would be if the employer or employee chose not to comply with the standard and the employee lost the sight of an eye, if not his life, in the event of an accident.

SUMMARY OF THE INVENTION

A sideshield eye protector is presented which includes a comfort and safety wing that is formed as a surface appendage thereon and extends in a generally perpendicular direction from the surface of the sideshield along the contoured edge of the sideshield positioned closest to the wearer's face. The comfort and safety wing may be integral to the sideshield forming an integral structure therewith or removably attached thereto. The comfort and safety wing is oriented generally parallel with the facial surfaces and generally follows the proximate facial contours. A separate wing portion may be fabricated on both the upper and lower parts of each sideshield, the upper wing portion extending from upper contoured edge of the sideshield which provides additional coverage over the upper portion of the eye orbits, temple and lower forehead area. The lower face about the lower eye orbit and upper cheek area has a generally parallel orientation with those facial surfaces

BRIEF DESCRIPTION OF THE DRAWINGS

The novel features believed characteristic of the present invention are set fourth in the appended claims. The invention itself, however, as well as a preferred mode of use, further objectives and advantages thereof, will be best understood by reference to the following detailed description of an illustrative embodiment when read in conjunction with the accompanying drawings wherein:

FIGS. 7A, 7B, and 7C are views of a generic embodiment of a comfort wing with attached comfort pad in accordance with exemplary embodiments of the present invention;

FIGS. 8A–8J are views of a reversibly engaging comfort pad and generic wing portion with various means for attachment thereon in accordance with exemplary embodiments of the present invention;

FIGS. 8A–8E are diagrams of cross-sectional views of the upper wing portion and comfort pad with various means for attachment in accordance with exemplary embodiments of the present invention;

FIGS. 10A–10D are views depicting a removably attachable comfort wing in accordance with an exemplary embodiment of the present invention.

Other features of the present invention will be apparent from the accompanying drawings and from the following detailed description.

DETAILED DESCRIPTION OF THE INVENTION

Figure 1:
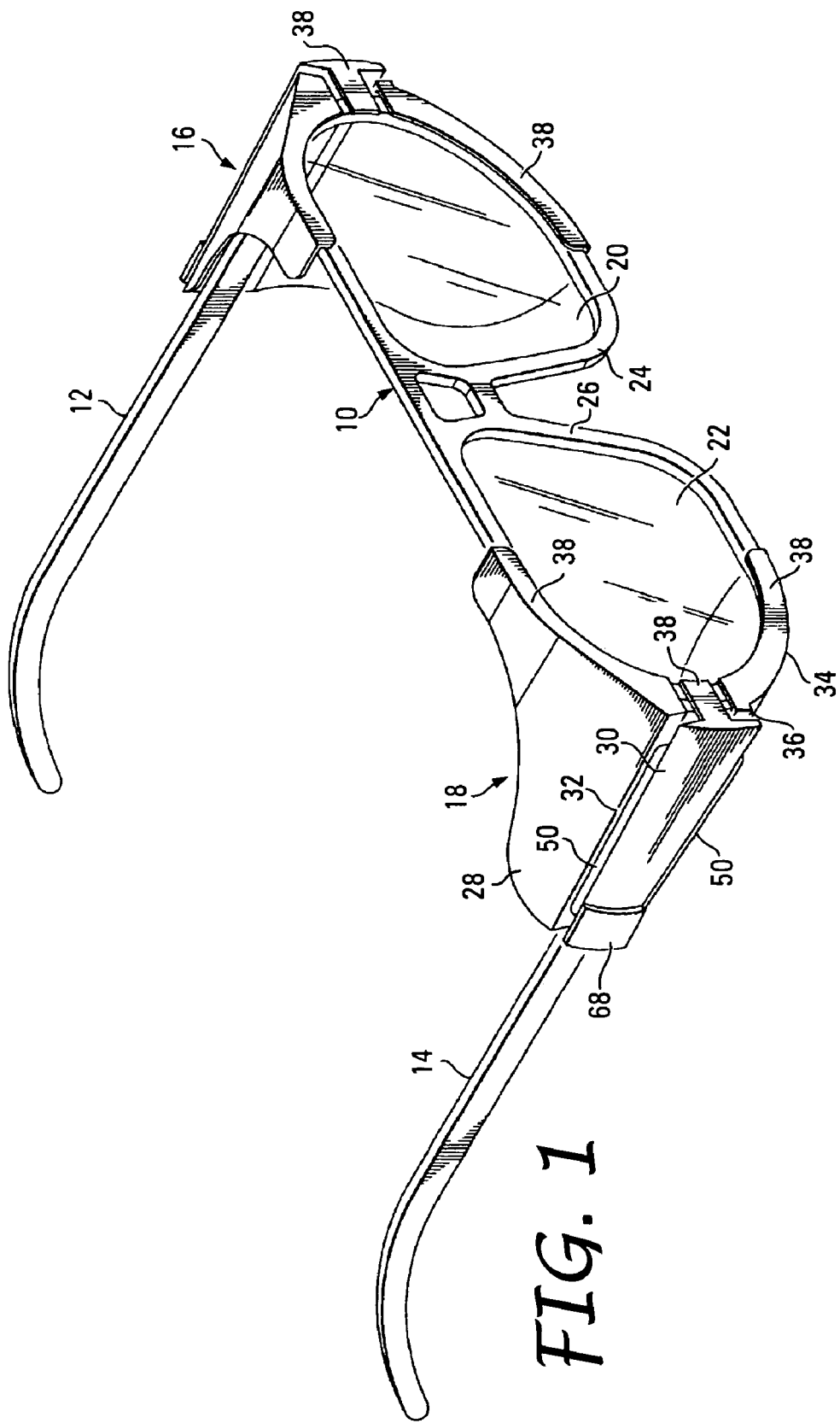
FIG. 1 is a partial isometric view of a pair of eyeglasses having the full sideshields removably attached to each side thereof as generally known in the prior art.

FIG. 1 is a partial isometric view of a pair of eyeglasses having the full sideshields removably attached to each side thereof as generally known in the prior art and described specifically in U.S. Pat. Nos. 5,748,278 and 6,393,609 issued to Bennie F. Simmons, Sr. and identified above. Briefly, eyeglass frame front portion 10 has temples 12 and 14 pivotally attached to each side thereof for holding the eyeglass frame front 10 on the face of a user. Full sideshields 16 and 18 are removably attached on each side of the frame front 10 and form a semicircle around the eyeglass lens 20 and 22 in front of the eye cavity of the user to provide eye protection on the top, bottom and side of the eye. As mentioned above, each sideshield 16 and 18 is a generally arcuate-shaped sideshield having a periphery for generally conforming to the shape of the individual eyeglass lens holders 24 and 26. Further, each of prior art sideshields 16 and 18 has a top portion 28 integrally formed to a side portion 30, along a first edge 32, and a bottom portion 34 integrally formed with side portion 30 at a second edge 36. As may be appreciated from the depiction in FIG. 1, the sideshields fitting each side of the eyeglass frame are mirror images of each other. As shown, a first flange portion 38 extends from at least one of the top portion 28, side portion 30, and bottom portion 34 at least partially in front of and substantially parallel to the eyeglass lens holder 26. Also, a second flange portion (not shown) may be included which extends inwardly from at least one of the top and bottom portions behind and substantially parallel to the eyeglass lens holder 26 to secure the eyeglass lens holder 26 between the first flange portion 38 and the second flange portion.

It should be noted that prior art sideshields 16 and 18 provide adequate protection for the wearer for a conventional safety frame which has a vertical dimension greater than 45.0 mm (1.77 in.). This particular sideshield design offers superior results when tested under the steel projectile test mandated by AMERICAN NATIONAL STANDARD Z87.1, Practice For Occupational and Educational Eye And Face Protection when affixed to conventional, non-fashion safety eyewear and does, in fact, provide excellent results when tested on safety fashion eyewear with a similar vertical dimension.

However, as with many government mandated safety tests, the projectile test does not accurately reflect projectile impacts in a real-world setting and, in the case of fashion oriented safety frames, portrays an overly optimistic result. The disparity in the projectile test and real-world incidents occur from the pragmatic realization that a safety glass wearer does not regularly ensure that the safety glasses are adjusted in the optimum protective position on the head, one that mimics the positioning used for the projectile test. Often the safety glasses slide down the wearer's face increasing the likelihood of a direct impact to the eyes from a projectile. As the vertical dimension of the frames decreases to accommodate fashion trends, the likelihood of exposure increases as does the incidence of injury that could otherwise have been prevented.

Figure 2:
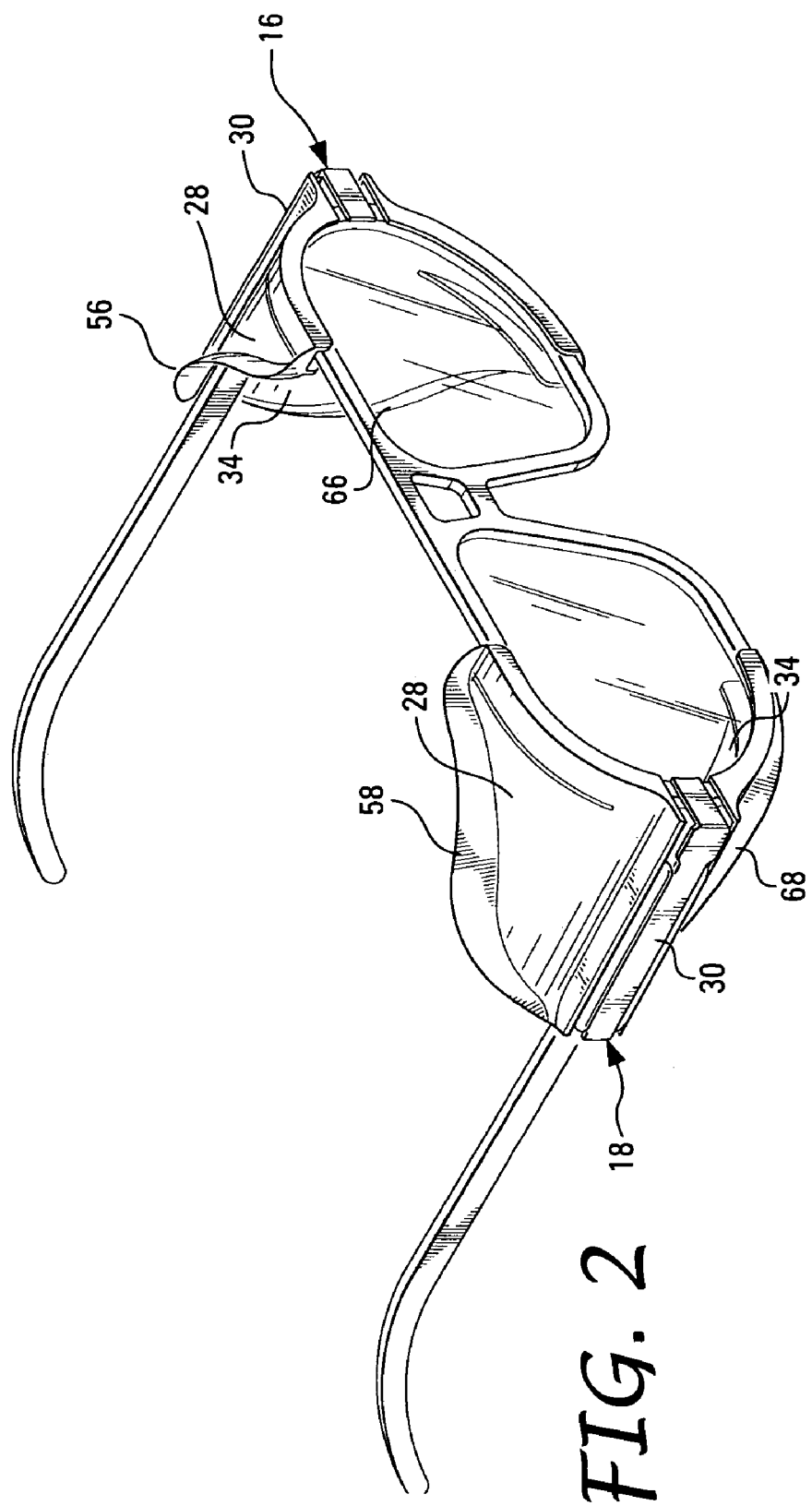
FIG. 2 is a partial isometric view of a pair of eyeglasses having the full sideshields removably attached to each side thereof, wherein each sideshield further includes comfort and safety wing portions in accordance with an exemplary embodiment of the present invention for supplementing the side protection and comfort to the wearer.

FIG. 2 is a partial isometric view of a pair of eyeglasses having the full sideshields removably attached to each side thereof as generally known in the prior art, but further including comfort and safety wings in accordance with an exemplary embodiment of the present invention. The safety wings supplement the wearer's protection from projectiles by, for instance, increasing the coverage area around the eyes and eye orbit areas over the side protection offered by prior art sideshields by extending the vertical coverage of conventional sideshields. It should be noted that the particular type of sideshield used herein has been selected merely for contrast and is not meant to limit the practice of the present invention in any way. The design features of the sideshield itself are unimportant for the application of the presently-described safety and comfort wing, except for those features specifically discussed below. Full sideshields 16 and 18 depicted in FIG. 2 merely illustrate exemplary side protection used for purpose of describing the present invention.

The present sideshield and safety wing is typically formed from a polycarbonate material which may be transparent, absorptive or opaque and is generally arcuate-shaped having a periphery for generally conforming to the shape of the eyeglass frame and has a top portion, upper wing portion, a bottom portion, lower wing portion and may also have a separate side portion, integrally formed as a single unit.

With further regard to FIG. 2, each of left and right sideshields 16 and 18 has a top portion 28, a bottom portion 34 and a side portion 30, integrally formed therebetween. However, in accordance with other embodiments of the present invention, left and right sideshields 16 and 18 may be integrally formed from only top portion 28, and bottom portion 34, whereby the side portion is formed from the top and bottom portions. With specific regard to left sideshield 16 depicted in FIG. 2, top portion 28 extends curvilinearly upward from side portion 30, toward the wearer, ending in a curvilinear perimeter that generally follows the contour of a wearer's face. Upper comfort and safety wing portion 56 (hereinafter referred to as a "comfort wing" or more simply merely as a "wing") extends in a substantially upwardly vertical direction from the curvilinear perimeter edge of top portion 28, making a generally acute departure from the surface contour of top portion 28. Along some portions of the curvilinear perimeter of the top portion 28, wing portion 56 makes a generally perpendicular departure from the orientation of top portion 28. Upper wing portion 56 forms a surface which follows the contour of the curvilinear perimeter of top portion 28 in a generally vertical direction, thereby extending the protecting coverage of left sideshield 16 upwardly over the upper portion of the eye orbit, temple and lower forehead area. In its substantially upwardly vertical orientation, upper wing portion 56 maintains a substantially parallel orientation with the wearer's facial surfaces that are proximate to the wing.

Turning now to bottom portion 34 of left sideshield 16 as depicted in FIG. 2, lower wing portion 66 extends in a substantially downwardly vertical direction from the curvilinear perimeter edge of bottom portion 34, making a generally acute departure from the surface contour of bottom portion 34. Along some portions of the curvilinear perimeter of bottom portion 34, wing portion 66 makes a generally perpendicular departure from the orientation of bottom portion 34. Essentially, lower wing portion 66 forms a surface which follows the contour of the curvilinear perimeter of bottom portion 34 in a generally vertical direction, thereby extending the protecting coverage of left sideshield 16 downwardly over the lower eye orbit and upper cheek area and has a generally parallel orientation with those facial surfaces.

Correspondingly, upper and lower wing portions 58 and 68 of right sideshield 18 are also formed by extending the respective top and bottom portions 28 and 34 acutely outward, in places up to an approximate right angle to the respective top and bottom portions 28 and 34 in a similar manner as described immediately above for left sideshield 16.

Alternatively, in accordance with other exemplary embodiments of the present invention, the comfort wing may, rather than being configured as discrete upper and lower wing portions, be formed as a contiguous comfort wing extension to the surfaces of respective top portion 28, bottom portion 34, and side portion 30 of the sideshield. This embodiment may be understood as merely semantics because, while the comfort wing extends the coverage area of side portion 30, the comfort wing merely increases the extent of side portion 30 along its predefined surface contour, rather than forming a surface at an acute angle to it. Therefore, even though a sideshield may be configured with a contiguous comfort wing, the wing may still appear as two discrete wing portions; an upper portion and a lower portion.

Figure 3:
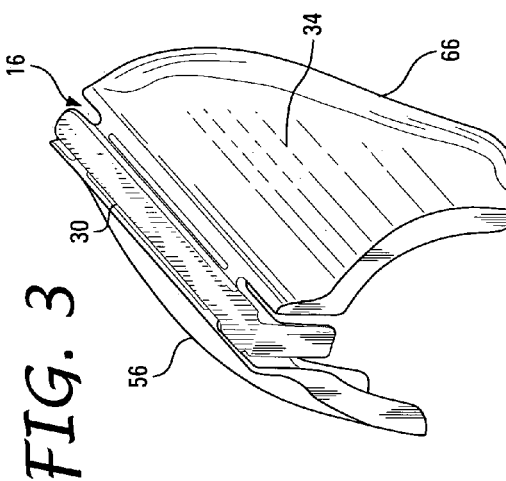
FIG. 3 is a diagram depicting an isometric view of a sideshield having upper and lower comfort and safety wings in accordance with an exemplary embodiment of the present invention.
Figure 5:
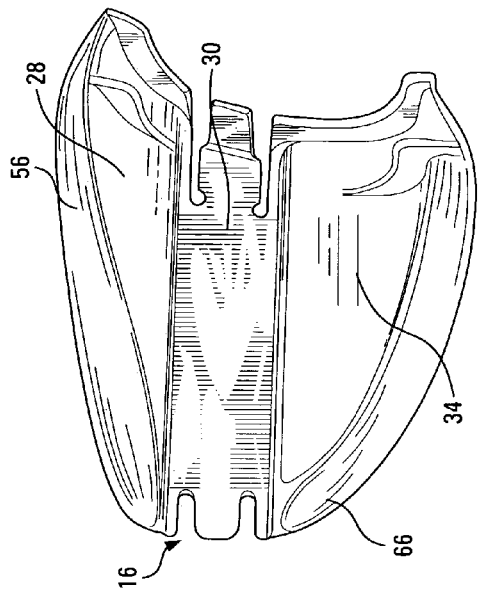
FIG. 5 is a diagram depicting an inside lateral view of a sideshield having upper and lower comfort and safety wings in accordance with an exemplary embodiment of the present invention.
Figure 4:
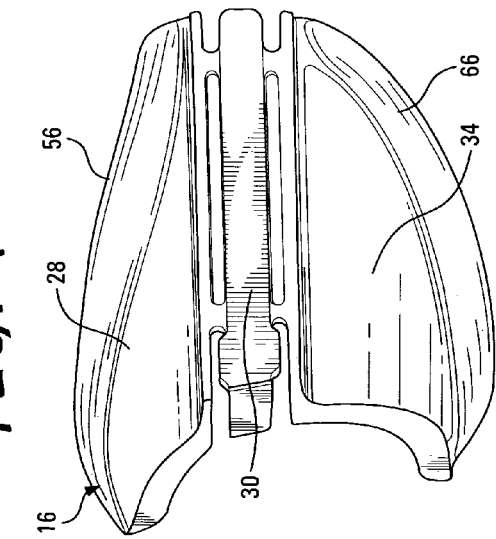
FIG. 4 is a diagram depicting an outside lateral view of a sideshield having upper and lower comfort and safety wings in accordance with an exemplary embodiment of the present invention.

The construction of an exemplary safety sideshields with comfort wing may be better appreciated with reference to the isometric view of left sideshield 16 showing upper wing portion 56 and lower wing portion 66 in FIG. 3, and the corresponding outside view in FIG. 4, and inside view of left sideshield 16 and wing portions in FIG. 5. It should be appreciated that right sideshield 18 with upper and lower wing portions 58 and 68 is a mirror image of left sideshield 16 with upper and lower wing portions 56 and 66. For that reason, the right side is not depicted separately in a figure from left sideshield 16.

Figure 6:
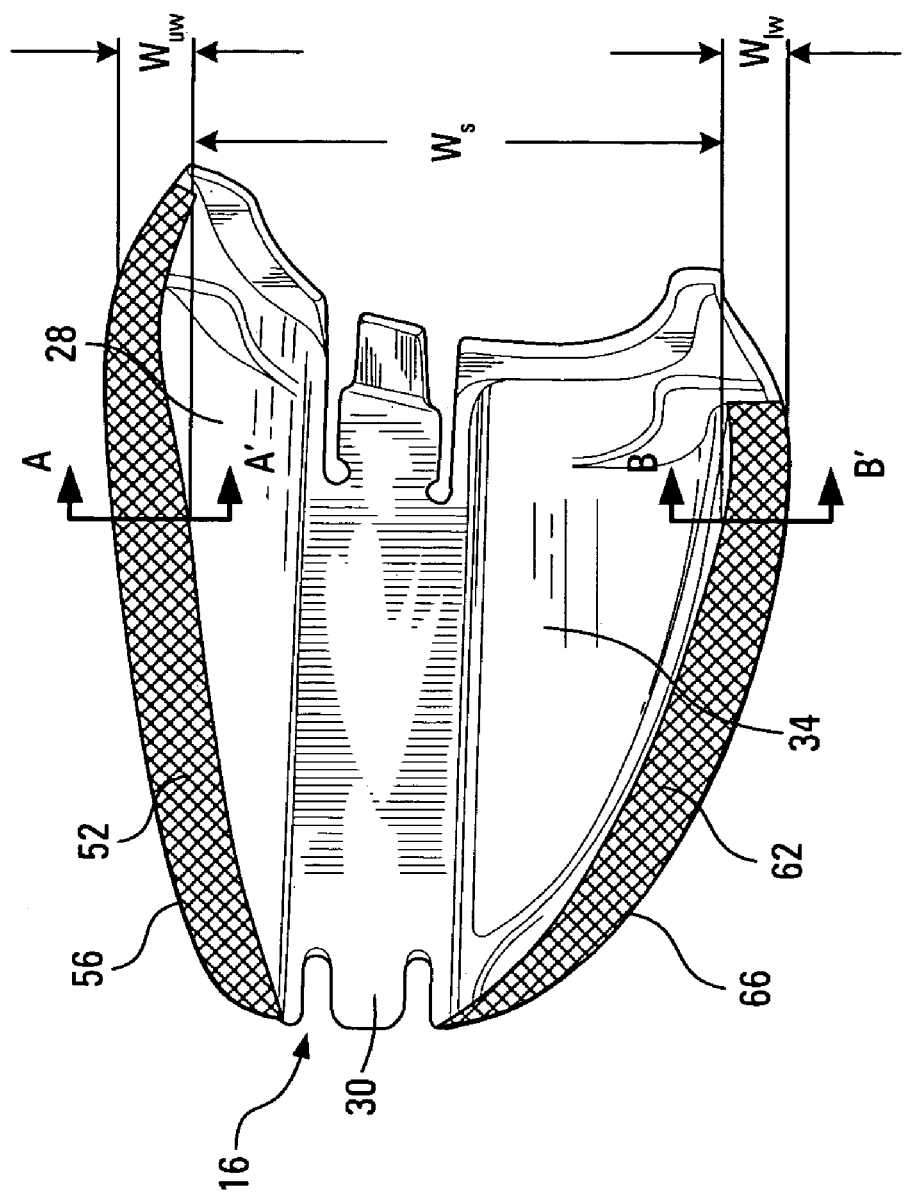
FIG. 6 is a diagram depicting a left sideshield as an inside view which includes a comfort pad in accordance with another exemplary embodiment of the present invention.

Safety sideshields incorporating comfort and safety wings provide an additional measure of protection for the wearer's eyes and face. The amount of added protection is quantifiable and is approximately equal to the width of the wing portion (that portion which is substantially vertical). Referring now to FIG. 6, left sideshield 16 is depicted as an inside view with upper and lower wing portions 56 and 66 in accordance with an exemplary embodiment of the present invention. Notice from FIG. 6 that upper and lower wing portions 56 and 66 increase the effective coverage of the sideshield because the surface of the wing portions project radially outward from sideshield 16 following the contour of the wearer's face. Thus, the wing configuration provides the maximum amount of added coverage area for the wing surface area.

Upper and lower wing portions 56 and 66 are specifically designed to give vulnerable facial structures, such as the eyes and eye sockets, substantially more protection than would be realized with bare sideshields.

In accordance with a further exemplary embodiment of the present invention, upper wing portion 56 is vertically wider than lower wing portion 66. In practical usage situations, safety glasses tend to slide down the wearer's nose from activity, perspiration and/or fatigue. When the glasses and sideshields are improperly positioned on a wearer's head, the wearer's eye is exposed to objects from any direction over the sideshields. Therefore, in accordance with an exemplary embodiment of the present invention, the vertical dimension of upper wing portion 56 is increased resulting in more upper coverage area to compensate for cases where the safety glasses have slid downward in an improper position. FIG. 6 is a diagram of a safety sideshield configured with upper and lower comfort wings wherein the upper comfort wing is widened to accommodate slippage and improper positioning. In the depicted illustration, upper wing portion 56 extends integrally upwardly from top portion 28, and lower wing portions 66 extends integrally downwardly from lower portion 34 as described elsewhere above. The coverage area of the respective upper and lower wing portions is depicted as the shaded area of sideshield 16, designated as upper coverage area 52 and lower coverage area 62, respectively. With particular attention to upper coverage area 52, it can be seen that maximum width, $W_{uw}$, of upper wing portion 56 is somewhat larger at cross section A–A' than the corresponding cross-section B–B' of lower wing portion 66, depicted as maximum width, $w_{lw}$. In accordance with one exemplary embodiment, maximum width, $w_{uw}$, of upper wing portion 56 is approximately 6.5 mm (0.26 in.), while maximum width, $w_{lw}$, of lower wing portion 66 is only 6.0 mm (0.24 in.) at the corresponding location. It should be understood that these vertical width measurements, and others allude to herein, are merely exemplary values used for the purpose of describing the present invention and not intended to limit the scope or usage of the present invention.

The importance of upper and lower wing portions 56 and 66 to safety sideshield 16 for protecting the wearer may be better understood by illustrative comparison with prior art sideshields. From the exemplary sideshield depicted in FIG. 6, it can be seen that the vertical coverage area of safety sideshield 16 with upper and lower wing portions 56 and 66 is larger with the comfort wings; however, what is not easily discernable from the figure is the magnitude of the additional coverage area in comparison to the coverage area of bare sideshield 16 without comfort wings. The vertical width of the safety sideshield coverage area without the comfort wings is shown as $W_s$. For fashion eyeglass frames, $W_s$ is approximately 35.0 mm (1.38. in.), though as discussed above, $W_s$ for conventional eyeglass frames may be substantially larger. Therefore, a typical prior art safety sideshield for fashion eyewear may be expected to protect a maximum of 35.0 mm vertically. If, as described in the example above, the maximum width $W_{lw}$ of lower wing portion 66 and maximum width $W_{uw}$ of upper wing portion 56 taken together offered only a nominal increase of 12.5 mm in vertical coverage, then the additional coverage of the comfort wings increases the vertical coverage by 37 percent over bare prior art sideshields. Thus, the presently-described invention will provide approximately 37 percent greater maximum vertical coverage over the prior art. Furthermore, the location of the additional coverage area from wing portions 56 and 66 corresponds to sensitive areas of the wearer's face that often need more protection. This is especially true for situations where the safety glasses are not adjusted properly on the wearer's head to their optimum protective position. It should be understood that the vertical dimensions of wing portions 56 and 66 ($W_{uw}$ and $W_{lw}$) and sideshield 16 ($W_s$) described above are exemplary values used only for describing the present invention. In practice, the maximum vertical width dimension $W_{uw}$ of the upper wing portion may range from 3.0 mm (0.12 in) to 20.0 mm (0.78 in), or greater, depending on the intended use in the environment; types of hazards normally present and severity of the risk to the wearer in the environment; the style and type of safety glasses, their fit, the likelihood of the particular style and type staying in place; the wearer's usage habits; and other safety related factors. The maximum vertical width dimension $W_{lw}$ of the lower wing portion also may range from 3.0 mm to 20.0 mm, or greater, depending on the above-mentioned factor. Typically, safety sideshields are fabricated with the maximum width dimension $W_{uw}$ of the upper wing portion which is somewhat larger than maximum width dimension $W_{lw}$ for the lower wing portion for the reasons discussed above.

Characteristically, sideshield manufacturers design sideshields so that the inner contoured edges of each sideshield follows the wearer's natural facial contour without actually coming in contact with the face itself. Manufacturers design this gap to serve several purposes. First, the gap allows persons with rounder, fuller faces to wear the sideshields in reasonable comfort. The gap also provides a distance offset for decelerating and absorbing impact energy. Contact points such as the bridge of the nose and ears absorb shock from a projectile impact before the inner contoured edges of the sideshield make contact with the wearer's face. The gap also serves to isolate the wearer from rough areas of the contoured edge that would irritate the wearer's face. The roughness results from the manufacturing molding process. Typically, manufacturers utilize multi-section molds that join together at the contoured edges of the workpiece. Plastic spurs and unconformities result on those edges from the small amounts of molten plastic seeping through the joint or misalignment of the molded sections. These spurs are easily polished off, but often manufacturers merely inspect a representative sample of the sideshields and then begins polishing only if the sample indicates a need for polishing.

In contrast with prior art sideshields, the sideshield and comfort wings of the present invention orient the contoured edges away from the wearer's face. Any incidental contact with the wearer is between the smoother inner surfaces (upper coverage area 52 and lower coverage area 62) of the sideshield wing portions rather than the rough, contoured edges.

In accordance with still another exemplary embodiment of the present invention, upper and lower comfort pads are secured to at least the inner surfaces of a portion of upper coverage area 52 and lower coverage area 62 of respective upper and lower wing portions 56 and 66. Notice from the diagram of sideshield 16 depicted in FIG. 6 that upper coverage area 52 and lower coverage area 62 each offer a convenient surface for attaching comfort strips or pads for added comfort. The pad offers a supple standoff for the wearer from sideshield 16. Comfort pads are depicted below in FIGS. 7 and 8.

FIGS. 7A, 7B, and 7C are views of a generic comfort wing with attached comfort pad in accordance with exemplary embodiments of the present invention. FIGS. 7A is a partial isometric view of a comfort wing portion with a comfort pad attached thereon. The diagrams illustrated in FIGS. 7B and 7C are cross-sectional views of the generic wing portion and comfort pad in accordance with exemplary embodiments of the present invention. With regard to FIG. 7A, a comfort wing is depicted that may be one of left upper wing portion 56, left lower wing portion 66, right upper wing portion 58, or right lower wing portion 68, and is represented generically in the figure as wing portion 40. Conforming to the shape of one of the inner surfaces of generic wing portion 40 is comfort pad 70. Comfort pad 70 is secured to the inner surface of wing portion 40 by adhesive 72. Adhesive 72 may be a permanent type of adhesive applied during the fabrication process, or it might instead be a temporary and reusable type of adhesive which allows the wearer to replace comfort pad 70 without discarding the entire sideshield.

FIG. 7B is a cross-sectional view of wing portion 40 with comfort pad 70 taken along line A–A' shown in FIG. 7A. Comfort pad 70 may be constructed in a variety of thicknesses, $D_{cp}$, depending on the intended application and the wearer's preference. In accordance with one exemplary embodiment of the present invention, comfort pad 70 has a thickness, $D_{cp}$, of approximately 5.0 mm (0.20 in.) for a wing thickness, $D_w$, of approximately 1.25 mm (0.05 in.). In practice, the value of $D_{cp}$ is selected based on the desired offset distance between the comfort wing and the wearer's face. Typically, comfort pad 70, $D_{cp}$ is between 3.0 mm (0.125 in.) and 6.0 mm (0.240 in.), but may be increased or decreased to accommodate a particular wearer.

Comfort pad 70 may be fabricated from a variety of soft and semi-soft rubber or plastic compounds that are comfortable and increase the shock absorbency for the sideshield. In accordance with this exemplary embodiment, comfort pad 70 is formed from a pliable material with a smooth outer surface for increased comfort, thus allowing comfort pad 70 to flexibly conform to the shape of the inner surface of wing portion 40 for easily placing and replacing the pad thereon. Because comfort pad 70 is bonded to a wing portion, the pad material need not be resilient enough to hold the shape of the inner surface of wing portion 40. However, in accordance with another exemplary embodiment, comfort pad 70 is formed from a pliable but resilient material which holds the shape of the inner surface of wing portion 40, while providing the needed comfort to the wearer. In that case, the permanent contour of the comfort pad will conform to one of two basic wing portion surface shapes: the upper left/upper right wing portions inner surface shape; and the lower right/lower left wing portions inner surface shape. In accordance with still another embodiment, comfort pad 70 may extend across the entire left or right sideshield; therefore, only two comfort pads would-be necessary. Exemplary pad materials include pressure sensitive one-sided foam rubber or pressure sensitive vinyl foam.

With particular regard to the shape of comfort pad 70, attention is directed to FIG. 2, FIG. 6 and FIGS. 7A and 7B. Notice from the figures that the inner surface of upper coverage area 52 has an outer perimeter shape that is unique from the outer perimeter shape of the inner surface of lower coverage area 62. Also, upper coverage area 52 is somewhat longer than lower coverage area 62. Therefore, the "fit" of comfort pad 70 to the coverage area of a wing portion depends on several factors, i.e., outer perimeter shape coincidence, vertical symmetry, and physical flexibility. In some cases, it may be desirable for comfort pad 70 to match a wing's outer perimeter coverage area, i.e., the outer perimeter shape of comfort pad 70 coinciding with that of the respective wing's outer perimeter coverage area. Consequently, the upper and lower comfort pad would not be interchangeable. Moreover, while the left and right safety sideshields are mirror images of one another, neither upper coverage area 52 nor lower coverage area 62 is vertically symmetrical, so the left and right comfort pads would not be interchangeable either. Thus, if it is desirable for the outer perimeter shape of the pad to coincide with that of the respective coverage areas, a typical pair of safety sideshields with comfort wings would require four uniquely shaped comfort pads. A comfort pad kit would then contain four distinctively shaped comfort pads. Also, while it is expected that comfort pad 70 may be formed from a pliable material which easily conforms to the surface shape of a wing, according to this embodiment the material may also be resilient enough to hold its shape since the pads are not interchangeable anyway, i.e., each of the four pads has a unique shape.

If the coincidence requirement is relaxed, then a kit may comprise only two pair of identically shaped comfort pads, a pair of identically shaped and interchangeable upper comfort pads, and a second pair of identically shaped and interchangeable lower comfort pads. Even though the left and right wings are mirror images of each other, the pads should still be pliable enough to conform to the inner surface of both of the wings, i.e., either the upper or the lower wings. If the pads are not pliable enough to easily conform to the curvilinear surface of both comfort wings (uppers or lowers), it might be necessary to use four uniquely shaped comfort pads to accommodate the unique shape of the individual comfort wings, notwithstanding the coincidence requirement for the outer perimeter shapes.

With regard to the least restrictive embodiment, comfort pad 70 may be formed from a pliable material in a single generic length and shape that is easily conformed to the unique curvilinear surface shape and perimeter of any of upper left wing 56, upper right wing 58, lower left wing 66 or lower right wing 68, while providing adequate coverage over the respective wing portion for comfort. In the generic case, a kit would comprise four identically shaped pliable comfort pads. Thus, depending on factors such as outer shape coincidence, vertical symmetry, and physical flexibility, a comfort pad kit will contain four pads having one, two, or four unique shapes.

In accordance with still another exemplary embodiment of the present invention, comfort pad 70, depicted in FIG. 7C, may include bladder 74 containing various materials for added comfort and shock absorbency. For example, the bladder may be filled with air, water, gel, or some other free-flowing or viscous substance, or a combination of the exemplary materials. Similar to the discussion of comfort pad 70 directly above, comfort pad 70 may be constructed to fit a pair of sideshields as kits comprising four uniquely shaped pads, two uniquely shaped pairs of pads, or four identical generically shaped pads composed of a pliable material.

In accordance with still other exemplary embodiments of the present invention, the comfort pad may be constructed to conform to more than a single surface of the wing, thereby eliminating or reducing the need for an adhesive to secure a comfort pad to a wing. Referring now to FIGS. 8A–8J, views of a reversibly engaging comfort pad and generic wing portion are shown with various means for attachment thereon in accordance with exemplary embodiments of the present invention. As was discussed above with regard to comfort pad 70, the reversibly engaging comfort pads depicted in FIGS. 8A–8J may be fabricated with any one of three types of pads set designs: four reversibly engaging comfort pads, each pad separately shaped to coincide with a particular comfort wing portion; two pair of identically shaped, reversibly engaging comfort pads, each pair interchangeably shaped to accommodate one of the upper comfort wings or the lower comfort wings; or four identically shaped, reversibly engaging comfort pads, each pad interchangeably shaped to accommodate any of the upper or lower comfort wing portions. However, in general, the comfort pads should be fabricated from a more resilient and less pliable material than is generally used for comfort pad 70 which is secured by adhesive bonding to ensure proper coupling with the coupling mechanism.

With regard to FIGS. 8A and 8B, reversibly engaging comfort pad 80 (alternatively referred to below as pad 80) is depicted proximate to generic wing portion 40. Wing portion 40, depicted in FIGS. 8A–8J, may be any one of the upper left, upper right, lower left and lower right wing portions designated as generic wing portion 40. In the same regard, the comfort pad depicted in FIGS. 8A–8J, shown as pad 80 in FIGS. 8A and 8B, may be a pad shape design in accordance with any one of the three types of comfort pad designs discussed immediately above, i.e., the four uniquely shaped, reversibly engaging comfort pad design; the two pair of two identically shaped, reversibly engaging comfort pad design; and the four identically shaped, reversibly engaging comfort pad design.

Figure 8B:
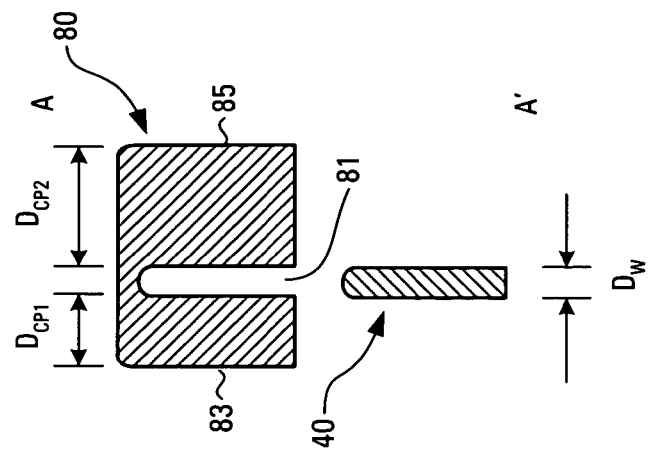
Figure 8A:
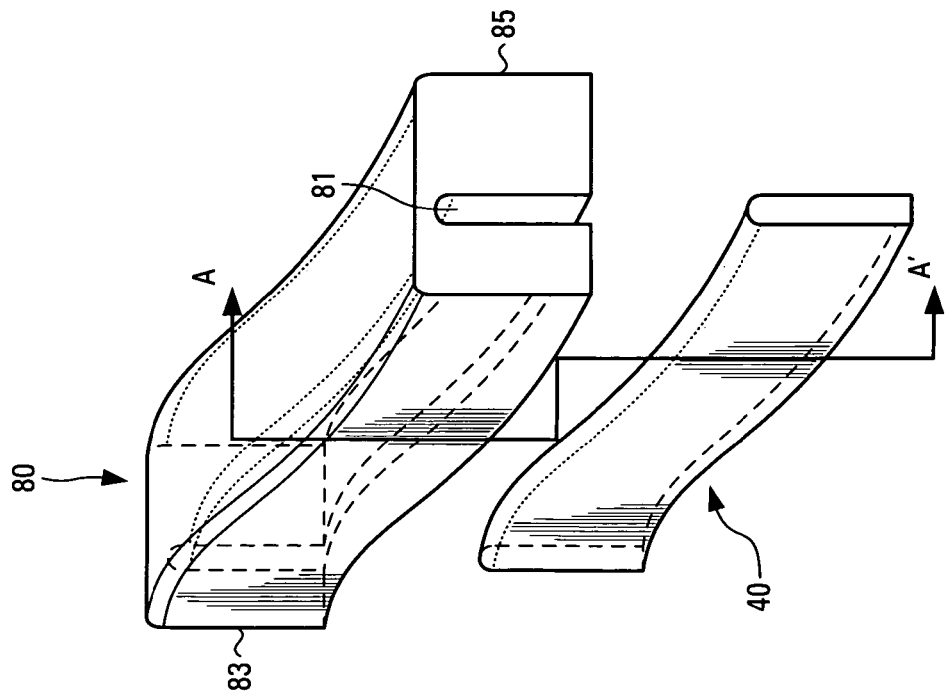

FIGS. 8A and 8B depict the least complicated coupling mechanism which utilizes friction to secure pad 80 to wing portion 40. With specific regard to FIG. 8A, a partial isometric view of comfort wing portion 40 with reversibly engaging comfort pad 80 is depicted in accordance with an exemplary embodiment of the present invention. Pad 80 is elongated having a first outer surface 83 and a second outer surface 85 disposed on either side of channel 81. In accordance with this exemplary embodiment, the U-shaped cross-sectional design of pad 80 enables the pad to grip wing portion 40 without any securing means other than friction along the contact surfaces of wing portion 40 against the outer surfaces of channel 81. The fit of wing portion 40 to channel 81 is shown more particularly in cross-sectional diagram FIG. 8B. The resiliency of pad 80 provides an additional securing force. Each of the exemplary embodiments depicted in FIGS. 8A–8J illustrates a mechanical coupling mechanism that is not-intended to use an adhesive. If, however, additional hold is desired, an adhesive may be used in conjunction with the coupling mechanism, for example, applied along a surface of channel 81. Exemplary pad materials include PVC (Polyvinyl Chloride), TPE (Thermal Plastic Elastomer) or TPR (Thermal Rubber Elastomer).

The lateral extents of channel 81 are generally shown as being open-ended, but in accordance with an alternative embodiment (not shown), may be closed for coupling to the lateral extents of wing portion 40. In that case, pad 80 is secured to wing portion 40 by the closed ends of channel 81 on pad 80 elastically gripping the outer ends of wing portion 40, in addition to the friction fit of wing portion 40 in channel 81.

It should also be appreciated that the reversibility feature of comfort pad 80 provides the wearer with an uncomplicated means for adjusting or customizing the fit of the sideshield and comfort wing to the unique shape of the wearer's facial structure. Turning now to FIG. 8B, a cross-sectional view of pad 80 and wing portion 40 is depicted at line A–A' shown on FIG. 8A. Notice that outer surface 83 is offset from channel 81 by a standoff distance of $D_{cp1}$, and outer surface 85 is offset from channel 81 by a standoff distance of $D_{cp2}$. Notice also from the depicted comfort pad in the illustration that distance $D_{cp1}$ is smaller than distance $D_{cp2}$. In accordance with another exemplary embodiment of the present invention, the reversibly engaging comfort pads are transposable for reversibly engaging one of the upper comfort wing portions and the lower wing portions. Reversibility enables a wearer to reverse the orientation of pad 80 such that either of first outer surface 83 or second outer surface 85 is directed inwardly toward the wearer's face by merely reversing the placement of the upper pads from, for example, the left upper wing to the right upper wing, while maintaining the vertical orientation channel 81. The same basic procedure can be followed for reversing the lower set of pads. By reversing the orientation of comfort pad 80 on wing portion 40, the offset, or standoff distance between the wearer's face and the sideshield assembly, can be altered to allow a wearer with virtually any shape of face to wear the sideshields in reasonable comfort. In accordance with one exemplary embodiment of the present invention, first standoff distance $D_{cp1}$, separating first outer surface 83 from channel 81, is approximately 3.0 mm (0.12 in.), and second standoff distance $D_{cp2}$, which separates second outer surface 85 from channel 81, is approximately 5.0 mm (0.20 in.). The diameter, $D_w$, of channel 81 is approximately 1.25 mm (0.05 in.).

Reversibly engaging pads 80 may be offered as kits having various sizes, thus allowing a wearer to custom fit the sideshield to his uniquely shaped face. In practice, standoff distance $D_{cp1}$ and standoff distance $D_{cp2}$ are typically between 2.0 mm (0.08 in.) and 6.0 mm (0.24 in.), but might be larger or smaller to accommodate some wearers. Reversibly engaging pad 80 should be designed for interchangeably accommodating either the upper wing portions or the lower wing portions, i.e., the two pair of two identically shaped pad design, for retaining the reversibility feature. One pair's shape interchangeably conforms to the shape of the surface of the upper wing portions and the other pair's shape interchangeably conforms to the shape of the surface of the lower wing portions. In certain situations, it may be possible for reversibly engaging pad 80 to have a generic shape design to reversibly engage any of the four wing portions and still retain the reversibility feature.

A comfort pad kit typically consists of a set of four comfort pads in any of the shape designs described above, with each pad having matched values for standoff distances $D_{cp1}$ and $D_{cp2}$. Alternatively, a kit may include multiple sets of four pads, with each set of pads having matched distance $D_{cp1}$ and $D_{cp2}$ values unique to that set. Using that type of kit, a wearer can fine-tune the fit by comparing the feel of sets of comfort pads with different standoff distances. Furthermore, a pad kit for a set of sideshields may consist of as few as two pads, one for the entire left sideshield and another for the entire right sideshield. Comfort pads 70, described above, is one type pad design that will readily accommodate the entire extent of a sideshield. However, it is much more difficult to configure the type of pad that uses a mechanical coupling mechanism for an entire sideshield, e.g., such as reversibly engaging pad 80. The frame of the glasses interferes with the fit of the pad at side portion 30.

Since FIGS. 8C and 8D illustrate substantially the same view of reversibly engaging comfort pad 82 on wing portion 40 depicted in FIGS. 8A and 8B for pad 80, only the differences between the embodiments will be discussed in detail. In the illustration, the channel of comfort pad 82 is modified by the inclusion of a bulbous portion of the terminating depth of channel 81, depicted as bulbous cavity 92F. The pliable nature of the material of comfort pad 82 compresses, thereby allowing the larger diameter of bead 92M to traverse channel 81. Coupling the pad over the wing is accomplished when bulbous cavity 92F receives and cooperates with bead 92M formed along the upper extent of wing portion 40. Uncoupling comfort pad 82 from wing portion 40 is accomplished by merely pulling the comfort pad 40 away from the wing portion.

FIGS. 8E and 8F illustrate still another mechanism for mechanically securing reversibly engaging pad 84 to wing portion 40 in accordance with an exemplary embodiment of the present invention. In accordance with this exemplary embodiment, one or more male pins 94M are fashioned onto the outer surface of wing portion 40 which is oriented outward from the wearer's face during usage. One or more cooperating orifices 94F are fabricated in comfort pad 84 for receiving and cooperating with male pins 94M. Male pins 94M and cooperating orifices 94F are positioned on the respective parts such that they couple together when pad 84 is installed on wing portion 40. Essentially, channel 81 of reversibly engaging pad 84 conforms male pins 94M in the same manner as described above, thereby allowing male pins 94M to be coupled into respective cooperating orifices 94F. It is expected that comfort pad 84 could be secured to either an upper or lower wing portion with as few as two pins, but more pins should be included for softer and less rigid pad materials. However, to ensure the reversibility of pad 84 onto wing 40, orifices 94F should be disposed symmetrically along channel 81 on other side of the centerline of pad 84. The placement of male pins 94M on wing 40 should also be disposed symmetrically on either side of an imaginary line, usually the centerline, on wing 40. It may also be possible to use one pin/orifice pair in conjunction with a friction-fitting channel as described in FIGS. 8A and 8B above, and/or an adhesive. Uncoupling comfort pad 84 from wing portion 40 is accomplished as described above by merely pulling reversibly engaging pad 84 away from the comfort wing.

Figure 8H:
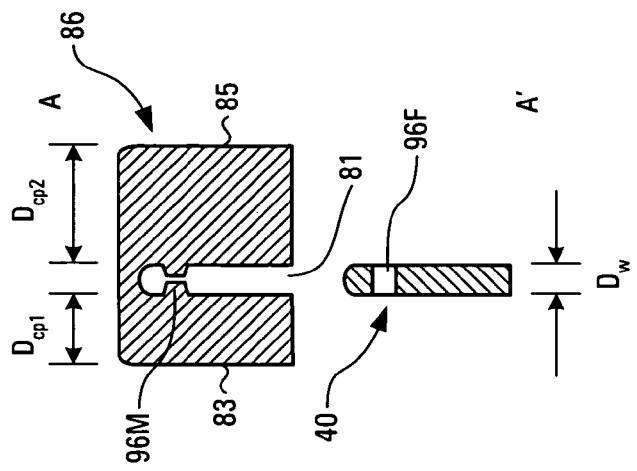
Figure 8G:
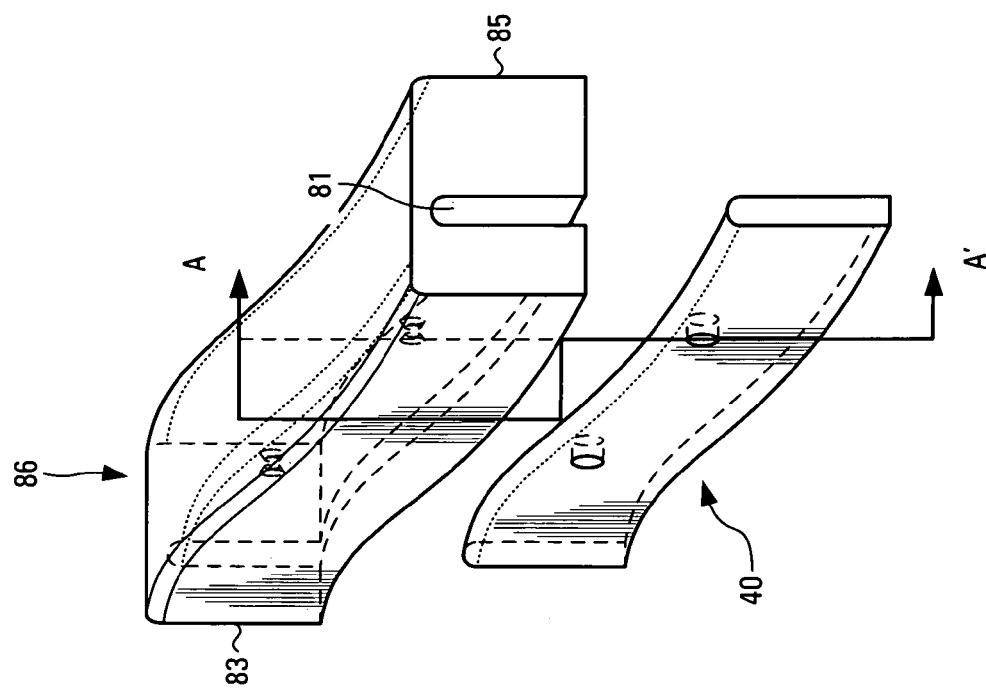

FIGS. 8G and 8H illustrate still another mechanism for mechanically securing reversibly engaging comfort pad 86 to wing portion 40 in accordance with an exemplary embodiment of the present invention. The underlying principle for the connection mechanism for this embodiment is essentially identical to the embodiment described in FIGS. 8E and 8F immediately above with the male and female cooperating parts being reversed. In accordance with this exemplary embodiment, one or more male dowels 96M are fashioned onto the outer surface of channel 81 in comfort pad 86. One or more cooperating orifices 96F are formed in or through wing portion 40. As in the embodiment described above, male dowels 96M and cooperating orifices 96F are positioned on the respective parts such that they couple together when comfort pad 86 is installed on wing portion 40. As depicted, male dowels 96M protrude from either side of the channel 84 in comfort pad 86, but may instead project from only one side of the channel. Here again, symmetric placement of the male dowels pins and cooperating orifices is necessary to assure reversibility.

Figure 8J:
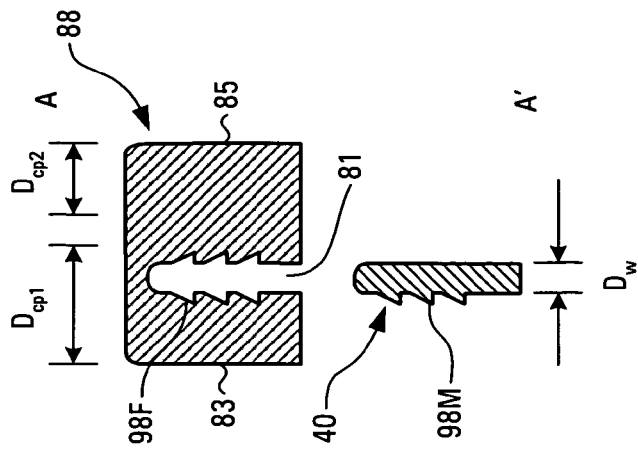
Figure 8I:
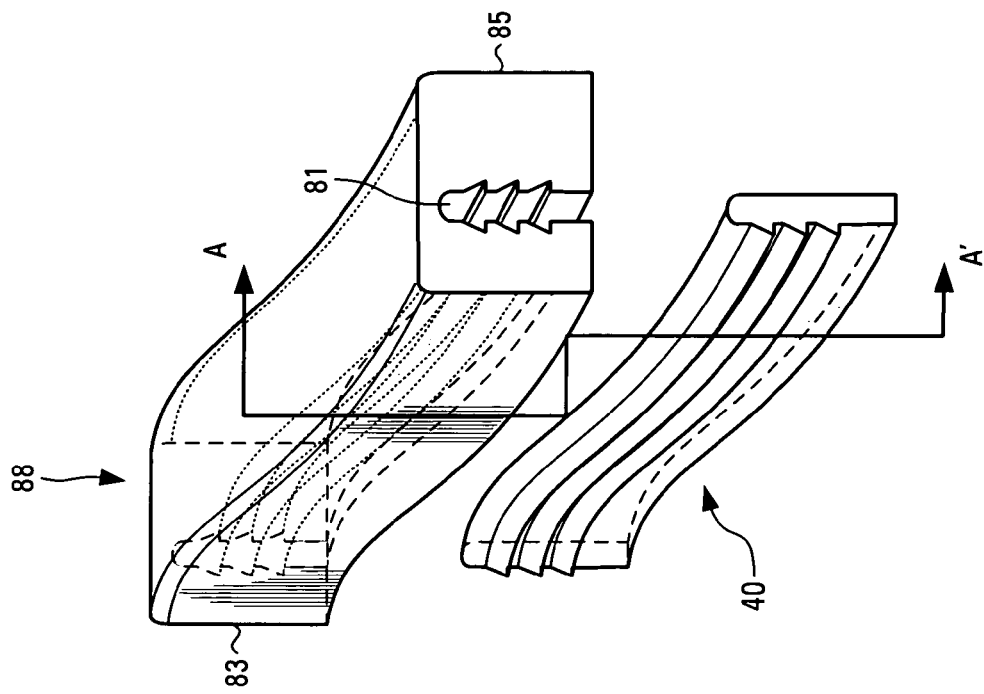

FIGS. 8I and 8J illustrate a lateral ridge coupling mechanism mechanically securing reversibly engaging pad 88 to wing portion 40 in accordance with an exemplary embodiment of the present invention. In accordance with this embodiment, one or more male ridges 98M are formed along the lateral extent of one side of wing portion 40, and when coupled to comfort pad 88, they cooperate with corresponding one or more grooves or lateral recesses 98F which follow the interior side walls of channel 81. The number and height of the ridges depend on the resiliency of the material used for fabrication comfort pad 88. However, lateral recesses 98F should be symmetrically disposed on either side of channel 81, while male ridges 98M should be placed only on the outer surface of wing 40 which is oriented away from the wearer's face while in use.

As mentioned generally herein, the safety sideshields may be a removable type safety sideshield, described above with regard to FIGS. 1–6, or a permanently mounted type of safety sideshield. Any of comfort pads 70, 80, 82, 84, 86 and 88 may be coupled to either a permanent or removable type of sideshield so long as the sideshield has a comfort wing that, if necessary, has the mechanical parts necessary for coupling.

A problem often associated with the permanent type of sideshields is that of being custom designed for accommodating a singular size and type of eyewear which generally offers the wearer an acceptable amount of protection, but usually little in the way of style and versatility. Permanent sideshields are generally integrated into the eyewear frames, usually making replacement impossible without disposing to the frames also. If a wearer wishes to upgrade the sideshields for any reason, the entire eyeglass and sideshield combination must be discarded in favor of the upgraded model. Upgrading permanent sideshields is an expensive proposition, and wearers often elect to delay replacing the sideshields until their current eyeglasses become non-functional or irreparably obsolete. A mere safety improvement to a sideshield is rarely sufficient motivation for wearers and employers to upgrade fully functional eyeglasses. The reluctance of wearers to upgrade is also common among owners of the removable type safety sideshields, but to a somewhat lesser extent because the cost associated with upgrading the removable type safety sideshield is much lower because the safety glasses need not be replaced. Therefore, in accordance with another exemplary embodiment of the present invention, removably attachable comfort wings are presented which may be installed on either the permanent type safety sideshield or the removable type safety sideshield and which provide substantially the same benefits as permanent comfort wings without the necessity of replacing either the sideshields or eyeglasses.

Figure 9:
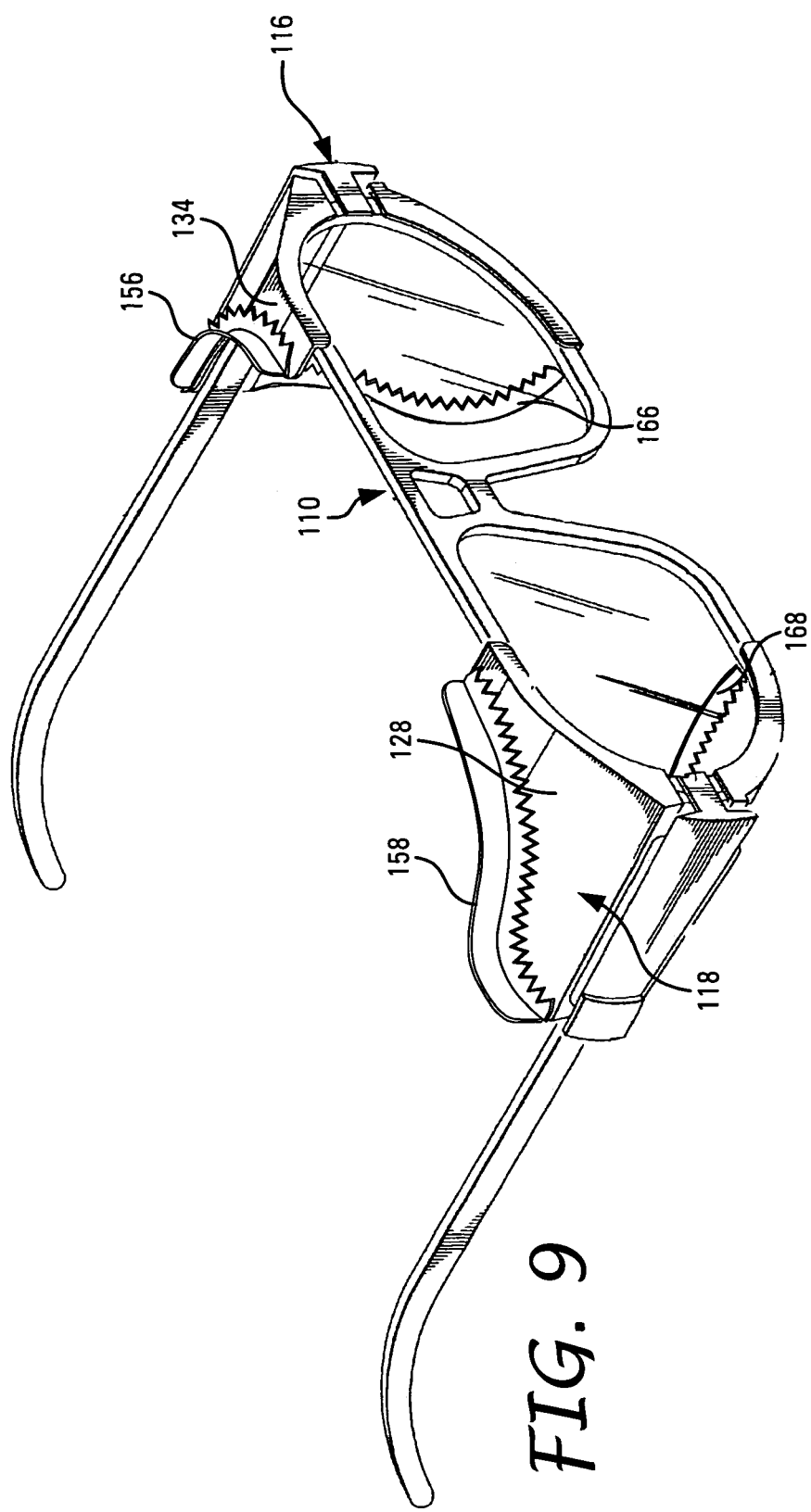
FIG. 9 is a partial isometric view of a pair of eyeglasses with sideshields incorporated on each side thereof as described generally above with regard to FIG. 1.

FIG. 9 is a partial isometric view of a pair of eyeglasses with sideshields incorporated on each side as generally described above in FIG. 1. Left and right sideshields 116 and 118 depicted therein may be either of a removable type safety sideshield, or a permanently mounted type of safety sideshield. In either case, removably attachable comfort wings 156, 158, 166 and 168 are removably secured to left and right sideshields 116 and 118 in accordance with an exemplary embodiment of the present invention. In the depicted illustration, removably attachable comfort wings 156 is shown attached to left upper surface 134 of left sideshields 116, removably attachable comfort wings 158 is shown attached to right upper surface 128 of right sideshields 118, and comfort wings 166 and 168 are shown attached to the respective left and right lower surfaces of the respective left and right safety sideshields 116 and 118. Removably attachable comfort wings 156, 158, 166 and 168 provide a convenient, inexpensive and easy-to-use means for upgrading any type of safety sideshields with comfort wings.

FIGS. 10A–10D are views depicting removably attachable comfort wing 150 in accordance with an exemplary embodiment of the present invention. FIG. 10A is a partial isometric view of a removably attachable comfort wing portion, and the diagrams in FIGS. 10B, 10C and 10D are top and side cross-sectional and frontal views of the comfort wing portion in accordance with exemplary embodiments of the present invention. Removably attachable comfort wings 150 comprise wing portion 152 which is integrally formed to upper retaining lip portion 154U and lower retaining lip portion 154L, whereby the wing and retaining lips are generally formed as a single unit. Removably attachable comfort wing 150 is secured to an edge of surface 160 (generically referring to any of the upper left, upper right, lower left and lower right sideshield surfaces) of a conventional safety sideshield without any securing means other than friction between surface 160 contacting the inner surfaces of upper and lower retaining lip portions 154U and 154L. Alternatively, an adhesive may be applied to the inner surfaces of upper and lower retaining lip portions 154U and 154L for securing to wing portion 152. In either case, wing portion 152 is oriented outwardly away from the wearer's eye area in a manner similar to that discussed above for comfort wings integrally formed as a single unit to the sideshield. However, in accordance with this embodiment, removably attachable comfort wings 150 are intended for use with prior art sideshields without comfort wings. Thus, the added comfort and safety afforded by the present comfort wing may be afforded to virtually anyone with prior art safety sideshields without having to buy safety sideshields with comfort wings.

In further accordance with an exemplary embodiment of the present invention, removably attachable comfort wing 150 is flexibly configured to conform to the contoured edges of surface 1260 associated with either upper or lower surfaces on the left or right safety sideshield, while being resilient enough to protect the wearer's eyes from projectiles. This is accomplished by providing added flexibility for bending comfort wing 150 about the curved edge of a sideshield by incorporating relief ridges in upper and lower retaining lip portions 154U and 154L. These ridges absorb the bending stress and allow comfort wing 150 to bend smoothly to accommodate virtually any shape of the sideshield edge. Moreover, comfort wing 150 can be inverted for attachment to upper or lower sideshield surfaces. Thus, when provided as a kit, a set of comfort wings 150 may be comprised of identical comfort wings which removably attach to various surfaces on the safety sideshield. Comfort wings 150 are easily trimmed with a sharp blade and may be therefore somewhat longer than necessary and trimmed to fit by the wearer. Alternatively, a kit may instead contain a continuous length of comfort wing 150 that may be trimmed to fit by the wearer. The vertical extent of wing portion 152, $W_w$, may range from 3.0 mm (0.12 in) to 20.0 mm (0.78 in), or greater, depending on the intended use in the environment; types of hazards normally present and severity of the risk to the wearer in the environment; the style and type of safety glasses, their fit, the likelihood of the particular style and type staying in place; the wearer's usage habits; and other safety related factors. However, it should be recognized that the flexibility of wing portion 152 will be diminished somewhat with wider wings.

In accordance with still another embodiment of the present invention, comfort pad 170 may be optionally secured to the inner surface of wing portion 152 as described above in FIGS. 7A–7C. As a practical matter, comfort pad 170 interferes with the flexible removably attachable comfort wing 150 and is therefore normally attached to the inner surface of wing portion 152 after removably attachable comfort wing 150 has been affixed to the sideshields.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention and the practical application, and to enable others of ordinary skill in the art to understand the invention for various embodiments with various modifications as are suited to the particular use contemplated.

What is claimed is:

1. A removably attachable comfort wing for use with a sideshield employed for use with an eyeglass frame having a pair of spaced eyeglass lens holders, said sideshield having a generally arcuate-shaped shield member comprising at least a top portion and a bottom portion, each of said top portion and said bottom portion having an inner surface and an outer surface, said top portion and said bottom portion each being defined by facial feature approximation contour, wherein a facial feature approximation contour of said top portion approximates a facial contour of at least a portion of one of a wearer's upper eye orbit and lower forehead, while a facial feature approximation contour of said bottom portion approximates a facial contour of at least a portion of one of a wearer's lower eye orbit and upper cheek, said removably attachable comfort wing comprising:
    a wing portion, said wing portion having a first surface and a second surface, said first surface and said second surface having a lateral edge defining an extent of said surfaces; and
    a selectively releasable coupling affixed to said wing portion for removably attaching to one of the top portion and the bottom portion of the sideshield, said selectively releasable coupling comprising:
        a first retention lip, said first retention lip having a first retention lip lateral edge, said first retention lip lateral edge being affixed to said first surface of said wing portion, and the first retention lip further comprises a plurality of relief ridges, said plurality of relief ridges being formed in an edge of said first retention lip opposite said first retention lip lateral edge;
        a second retention lip, said second retention lip having a second retention lip lateral edge, said second retention lip lateral edge being affixed to said first surface of said wing portion between said lateral edge, and said first retention lip; and
        a retention gap formed between said first retention lip and said second retention lip, wherein said removably attachable comfort wing is removably attached to one of said top portion and said bottom portion of said sideshield.

2. The removably attachable comfort wing recited in claim 1 above, wherein said second retention lip further comprises:
    a second plurality of relief ridges, said second plurality of relief ridges being formed in an edge of said second retention lip opposite said second retention lip lateral edge.

3. The removably attachable comfort wing recited in claim 1, wherein the selectively releasable coupling affixed to said wing portion, further comprises:
    an adhesive agent.

4. The removably attachable comfort wing recited in claim 1, wherein the selectively releasable coupling affixed to said wing portion, further comprises:
    an adhesive, said adhesive applied on a surface of one of said first retention lip and said second retention lip, said surface oriented toward said retention gap.

5. The removably attachable comfort wing recited in claim 1 above, wherein said one of said top portion and said bottom portion being on one of a left sideshield and a right sideshield.

6. The removably attachable comfort wing recited in claim 1 above, said removably attachable comfort wing being flexible for conforming to said one of said top portion and said bottom portion.

7. The removably attachable comfort wing recited in claim 1 above, wherein a lateral length being greater than a length of said one of said top portion and said bottom portion, whereby said lateral length of said removably attachable comfort wing is trimmed to the length of said one of said top portion and said bottom portion.

8. The removably attachable comfort wing recited in claim 1 above, further comprises:
    a removably attachable comfort pad, affixed to said inner surface of said removably attachable comfort wing.

9. The removably attachable comfort wing recited in claim 8 above, wherein said comfort pad further comprises:
    a solid core.

10. The removably attachable comfort wing recited in claim 8 above, wherein said comfort pad further comprises:
    a bladder, said bladder holding a viscose fluid.

11. The removably attachable comfort wing recited in claim 8 above, wherein said comfort pad further comprises:
    a U-shaped cross-section, wherein said comfort pad cooperates with an outer surface and an inner surface of said comfort wing.

12. The removably attachable comfort wing recited in claim 8 above further comprises:
    an adhesive interspersed between the said comfort pad and said inner surface of said comfort wing.

13. The removably attachable comfort wing recited in claim 8 above, wherein said comfort pad being shaped to cooperate with any of an upper removably attachable comfort wing for use with a left eye, an upper removably attachable comfort wing for use with a right eye, a lower removably attachable comfort wing for use with a left eye, and a lower removably attachable comfort wing for use with a right eye.

14. The removably attachable comfort wing recited in claim 8 above, wherein said removably attachable comfort pad being shaped to cooperate with any two of an upper removably attachable comfort wing for use with a left eye, an upper removably attachable comfort wing for use with a right eye, a lower removably attachable comfort wing for use with a left eye, and a lower removably attachable comfort wing for use with a right eye.

15. The removably attachable comfort wing recited in claim 8 above, wherein said comfort pad being shaped to cooperate with any one of an upper removably attachable comfort wing for use with a left eye, an upper removably attachable comfort wing for use with a right eye, a lower removably attachable comfort wing for use with a left eye, and a lower removably attachable comfort wing for use with a right eye.

16. The removably attachable comfort wing recited in claim 8 above, wherein said generally arcuate-shaped shield member forming a portion of a separately removable sideshield.

17. The removably attachable comfort wing recited in claim 16 above, wherein the sideshield being adaptable for use on safety glasses.

18. The removably attachable comfort wing recited in claim 16 above, wherein the sideshield being adaptable for use on safety goggles.

19. The removably attachable comfort wing recited in claim 16 above, wherein the sideshield being adaptable for use on glasses having transparent lenses.

20. The removably attachable comfort wing recited in claim 16 above, wherein the sideshield being adaptable for use on sunglasses.

21. The removably attachable comfort wing recited in claim 8 above, wherein said generally arcuate-shaped shield member forms a portion of a fixed sideshield.

22. The removably attachable comfort wing recited in claim 21 above, wherein the sideshield being affixed to safety glasses.

23. The removably attachable comfort wing recited in claim 21 above, wherein the sideshield being affixed to safety goggles.

24. The removably attachable comfort wing recited in claim 21 above, wherein the sideshield being affixed to corrective glasses.

25. The removably attachable comfort wing recited in claim 21 above, wherein the sideshield being affixed to sunglasses.

26. The removably attachable comfort wing recited in claim 1 above, wherein said removably attachable comfort wing having a width greater than two millimeters.

27. The removably attachable comfort wing recited in claim 1 above, wherein said removably attachable comfort wing formed from a resilient class of polycarbonate materials.

28. The removably attachable comfort wing recited in claim 1 above, wherein an eyeglass lens in one of said pair of spaced eyeglass lens holders is transparent.

29. The removably attachable comfort wing recited in claim 1 above, wherein an eyeglass lens in one of said pair of spaced eyeglass lens holders is semi-transparent.

30. A removably attachable comfort wing for use with a sideshield employed for use with an eyeglass frame having a pair of spaced eyeglass lens holders, said sideshield having a generally arcuate-shaped shield member comprising at least a top portion and a bottom portion, each of said top portion and said bottom portion having an inner surface and an outer surface, said top portion and said bottom portion each being defined by facial feature approximation contour, wherein a facial feature approximation contour of said top portion approximates a facial contour of at least a portion of one of a wearers upper eye orbit and lower forehead, while a facial feature approximation contour of said bottom portion approximates a facial contour of at least a portion of one of a wearers lower eye orbit and upper cheek, said removably attachable comfort wing comprising:

a selectively releasable coupling for removably attaching the comfort wing to one of the top portion and the bottom portion of a sideshield; and a wing portion affixed to said selectively releasable coupling, said wing portion comprises a first surface and a second surface, and further comprise a first lateral edge and a second lateral edge, the first and the second lateral edges define the boundaries of the first and the second surfaces, wherein at least one of the first surface and the second surface being affixed to said selectively releasable coupling proximate to the second lateral edge, and said first and said second lateral edges each form a continuous contour having a cumulative arc length of less than 360 degrees.

31. The removably attachable comfort wing recited in claim 30, wherein the selectively releasable coupling affixed to said wing portion, further comprises:

an adhesive agent.

32. The removably attachable comfort wing recited in claim 30 above, wherein said one of said top portion and said bottom portion being on one of a left sideshield and a right sideshield.

33. The removably attachable comfort wing recited in claim 30 above, said removably attachable comfort wing being flexible for conforming to said one of said top portion and said bottom portion.

34. The removably attachable comfort wing recited in claim 30 above, wherein a lateral length being greater than a length of said one of said top portion and said bottom portion, whereby said lateral length of said removably attachable comfort wing is trimmed to the length of said one of said top portion and said bottom portion.

35. The removably attachable comfort wing recited in claim 30 above further comprises:

a comfort pad, said comfort pad affixed to said inner surface of said removably attachable comfort wing.

36. The removably attachable comfort wing recited in claim 35 above, wherein said comfort pad further comprises:

a solid core.

37. The removably attachable comfort wing recited in claim 36 above, wherein said comfort pad further comprises:

a bladder, said bladder holding a viscose fluid.

38. The removably attachable comfort wing recited in claim 36 above, wherein said comfort pad further comprises:

a U-shaped cross-section, wherein said comfort pad cooperates with an outer surface and an inner surface of said comfort wing.

39. The removably attachable comfort wing recited in claim 36 above further comprises:

an adhesive interspersed between the said comfort pad and said inner surface of said comfort wing.

40. The removably attachable comfort wing recited in claim 36 above, wherein said comfort pad being shaped to cooperate with any of an upper removably attachable comfort wing for use with a left eye, an upper removably attachable comfort wing for use with a right eye, a lower removably attachable comfort wing for use with a left eye, and a lower removably attachable comfort wing for use with a right eye.

41. The removably attachable comfort wing recited in claim 30 above, wherein a removably attachable comfort pad being shaped to cooperate with any two of an upper removably attachable comfort wing for use with a left eye, an upper removably attachable comfort wing for use with a right eye, a lower removably attachable comfort wing for use with a left eye, and a lower removably attachable comfort wing for use with a right eye.

42. The removably attachable comfort wing recited in claim 30 above, wherein said comfort pad being shaped to cooperate with any one of an upper removably attachable comfort wing for use with a left eye, an upper removably attachable comfort wing for use with a right eye, a lower removably attachable comfort wing for use with a left eye, and a lower removably attachable comfort wing for use with a right eye.

43. The removably attachable comfort wing recited in claim 30 above, wherein the sideshield being adaptable for use on safety glasses.

44. The removably attachable comfort wing recited in claim 30 above, wherein the sideshield being adaptable for use on safety goggles.

45. The removably attachable comfort wing recited in claim 30 above, wherein the sideshield being affixed to corrective glasses.

46. The removably attachable comfort wing recited in claim 30 above, wherein the sideshield being affixed to sunglasses.

47. The removably attachable comfort wing recited in claim 30 above, wherein said removably attachable comfort wing having a width greater than two millimeters.

48. The removably attachable comfort wing recited in claim 30 above, wherein said removably attachable comfort wing formed from a resilient class of polycarbonate materials.

49. The removably attachable comfort wing recited in claim 30 above, wherein the selectively releasable coupling further comprises:
   a first retention lip, said first retention lip having a first retention lip lateral edge, said first retention lip lateral edge being affixed to said first surface of said wing portion;
   a second retention lip, said second retention lip having a second retention lip lateral edge, said second retention lip lateral edge being affixed to said first surface of said wing portion between said lateral edge, and said first retention lip; and
   a retention gap formed between said first retention lip and said second retention lip, wherein said removably attachable comfort wing is removably attached to one of said top portion and said bottom portion of said sideshield.

50. The removably attachable comfort wing recited in claim 49 above, wherein said first retention lip further comprises:
   a plurality of relief ridges, said plurality of relief ridges being formed in an edge of said first retention lip opposite said first retention lip lateral edge.

51. The removably attachable comfort wing recited in claim 50 above, wherein said second retention lip further comprises:
   a second plurality of relief ridges, said second plurality of relief ridges being formed in an edge of said second retention lip opposite said second retention lip lateral edge.

52. The removably attachable comfort wing recited in claim 49, wherein the selectively releasable coupling affixed to said wing portion, further comprises:
   an adhesive, said adhesive applied on a surface of one of said first retention lip and said second retention lip, said surface oriented toward said retention gap.

53. A removably attachable comfort wing for use with a sideshield employed for use with an eyeglass frame having a pair of spaced eyeglass lens holders, said sideshield having a generally arcuate-shaped shield member comprising at least a top portion and a bottom portion, each of said top portion and said bottom portion having an inner surface and an outer surface, said top portion and said bottom portion each being defined by facial feature approximation contour, wherein a facial feature approximation contour of said top portion approximates a facial contour of at least a portion of one of a wearers upper eye orbit and lower forehead, while a facial feature approximation contour of said bottom portion approximates a facial contour of at least a portion of one of a wearer's lower eye orbit and upper cheek, said removably attachable comfort wing comprising:
   a selectively releasable coupling for removably attaching the comfort wing to one of the top portion and the bottom portion of a sideshield; and
   a wing portion affixed to said selectively releasable coupling, said wing portion comprises a first surface and a second surface, and further comprise a first lateral edge and a second lateral edge, the first and the second lateral edges define the boundaries of the first and the second surfaces, wherein at least one of the first surface and the second surface being affixed to said selectively releasable coupling proximate to the second lateral edge, and each of said first lateral edge and said second lateral edge forming a concave contour and each of said first lateral edge and said second lateral edge forming a convex contour.

54. The removably attachable comfort wing recited in claim 53, wherein the selectively releasable coupling affixed to said wing portion, further comprises:
   an adhesive agent.

55. The removably attachable comfort wing recited in claim 53 above, wherein said one of said top portion and said bottom portion being on one of a left sideshield and a right sideshield.

56. The removably attachable comfort wing recited in claim 53 above, said removably attachable comfort wing being flexible for conforming to said one of said top portion and said bottom portion.

57. The removably attachable comfort wing recited in claim 30 above, wherein a lateral length being greater than a length of said one of said top portion and said bottom portion, whereby said lateral length of said removably attachable comfort wing is trimmed to the length of said one of said top portion and said bottom portion.

58. The removably attachable comfort wing recited in claim 30 above further comprises:
   a comfort pad, said comfort pad affixed to said inner surface of said removably attachable comfort wing.

59. The removably attachable comfort wing recited in claim 58 above, wherein said comfort pad further comprises:
   a solid core.

60. The removably attachable comfort wing recited in claim 59 above, wherein said comfort pad further comprises:
   a bladder, said bladder holding a viscose fluid.

61. The removably attachable comfort wing recited in claim 59 above, wherein said comfort pad further comprises:
   a U-shaped cross-section, wherein said comfort pad cooperates with an outer surface and an inner surface of said comfort wing.

62. The removably attachable comfort wing recited in claim 59 above further comprises:
   an adhesive interspersed between the said comfort pad and said inner surface of said comfort wing.

63. The removably attachable comfort wing recited in claim 59 above, wherein said comfort pad being shaped to cooperate with any of an upper removably attachable comfort wing for use with a left eye, an upper removably attachable comfort wing for use with a right eye, a lower removably attachable comfort wing for use with a left eye, and a lower removably attachable comfort wing for use with a right eye.

64. The removably attachable comfort wing recited in claim 53 above, wherein a removably attachable comfort pad being shaped to cooperate with any two of an upper removably attachable comfort wing for use with a left eye, an upper removably attachable comfort wing for use with a right eye, a lower removably attachable comfort wing for use with a left eye, and a lower removably attachable comfort wing for use with a right eye.

65. The removably attachable comfort wing recited in claim 53 above, wherein said comfort pad being shaped to cooperate with any one of an upper removably attachable comfort wing for use with a left eye, an upper removably attachable comfort wing for use with a right eye, a lower removably attachable comfort wing for use with a left eye, and a lower removably attachable comfort wing for use with a right eye.

66. The removably attachable comfort wing recited in claim 53 above, wherein the sideshield being adaptable for use on safety glasses.

67. The removably attachable comfort wing recited in claim 53 above, wherein the sideshield being adaptable for use on safety goggles.

68. The removably attachable comfort wing recited in claim 53 above, wherein the sideshield being affixed to corrective glasses.

69. The removably attachable comfort wing recited in claim 53 above, wherein the sideshield being affixed to sunglasses.

70. The removably attachable comfort wing recited in claim 53 above, wherein said removably attachable comfort wing having a width greater than two millimeters.

71. The removably attachable comfort wing recited in claim 53 above, wherein said removably attachable comfort wing formed from a resilient class of polycarbonate materials.

72. The removably attachable comfort wing recited in claim 53 above, wherein the selectively releasable coupling further comprises:
 a first retention lip, said first retention lip having a first retention lip lateral edge, said first retention lip lateral edge being affixed to said first surface of said wing portion;
 a second retention lip, said second retention lip having a second retention lip lateral edge, said second retention lip lateral edge being affixed to said first surface of said wing portion between said lateral edge, and said first retention lip; and
 a retention gap formed between said first retention lip and said second retention lip, wherein said removably attachable comfort wing is removably attached to one of said top portion and said bottom portion of said sideshield.

73. The removably attachable comfort wing recited in claim 49 above, wherein said first retention lip further comprises:
 a plurality of relief ridges, said plurality of relief ridges being formed in an edge of said first retention lip opposite said first retention lip lateral edge.

74. The removably attachable comfort wing recited in claim 50 above, wherein said second retention lip further comprises:
 a second plurality of relief ridges, said second plurality of relief ridges being formed in an edge of said second retention lip opposite said second retention lip lateral edge.

75. The removably attachable comfort wing recited in claim 49, wherein the selectively releasable coupling affixed to said wing portion, further comprises:
 an adhesive, said adhesive applied on a surface of one of said first retention lip gap.

* * * * *